US009074251B2

(12) United States Patent
Steemers et al.

(10) Patent No.: US 9,074,251 B2
(45) Date of Patent: Jul. 7, 2015

(54) LINKING SEQUENCE READS USING PAIRED CODE TAGS

(75) Inventors: Frank J. Steemers, Encinitas, CA (US); Kevin Gunderson, Encinitas, CA (US); Thomas Royce, San Diego, CA (US); Natasha Pignatelli, San Diego, CA (US); Igor Yu Goryshin, Madison, WI (US); Nicholas Caruccio, Madison, WI (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 13/080,345

(22) Filed: Apr. 5, 2011

(65) Prior Publication Data

US 2012/0208724 A1 Aug. 16, 2012

Related U.S. Application Data

(63) Continuation of application No. 13/025,022, filed on Feb. 10, 2011, now Pat. No. 8,829,171.

(51) Int. Cl.
*C12Q 1/68* (2006.01)

(52) U.S. Cl.
CPC .................................... *C12Q 1/6869* (2013.01)

(58) Field of Classification Search
None
See application file for complete search history.

(56) References Cited

U.S. PATENT DOCUMENTS

| | | | |
|---|---|---|---|
| 5,858,671 A | 1/1999 | Jones | |
| 5,965,443 A | 10/1999 | Reznikoff et al. | |
| 6,437,109 B1 | 8/2002 | Reznikoff et al. | |
| 6,593,113 B1 * | 7/2003 | Tenkanen et al. | 435/91.1 |
| 6,777,187 B2 | 8/2004 | Makarov et al. | |
| 6,828,098 B2 | 12/2004 | Langmore et al. | |
| 7,138,267 B1 | 11/2006 | Jendrisak et al. | |
| 7,537,897 B2 | 5/2009 | Brenner et al. | |
| 2004/0110191 A1 | 6/2004 | Winkler et al. | |
| 2004/0259229 A1 | 12/2004 | Thevelein et al. | |
| 2006/0040297 A1 | 2/2006 | Leamon et al. | |
| 2006/0216309 A1 * | 9/2006 | Holden | 424/200.1 |
| 2006/0292611 A1 | 12/2006 | Berka et al. | |
| 2009/0176234 A1 | 7/2009 | Dramanac et al. | |
| 2010/0069263 A1 | 3/2010 | Shendure et al. | |
| 2010/0120098 A1 | 5/2010 | Grunenwald et al. | |
| 2011/0311506 A1 * | 12/2011 | Craig | 424/94.5 |
| 2012/0208705 A1 | 8/2012 | Steemers | |

FOREIGN PATENT DOCUMENTS

| | | |
|---|---|---|
| WO | 2004/042078 | 5/2004 |
| WO | 2005/100585 | 10/2005 |
| WO | 2007/098279 | 8/2007 |
| WO | 2010/048605 | 4/2010 |

OTHER PUBLICATIONS

Jackson et al. Plasmid tagging for efficient large-scale sequence completion of entire clone inserts. BioTechniques, vol. 34, pp. 604-608, Mar. 2003.*
Kramer, Pr. cDNA library construction from single cells in Current Protocols in Neuroscience, 4.27.1-4.27-19, 2002.*
Xu, J. Extracting haplotypes from diploid organisms. Current Issues in Molecular Biology, vol. 8, pp. 113-122, Jul. 2006.*
Oh et al. A universal TagModule collection for parallel genetic analysis of microoganisms. Nucleic Acids Research, vol. 38, No. 14, p. e146, May 21, 2010, printed as pp. 1/14 to 14/14.*
Oh, J. A Robust Platform for High-Throughput Genomics in Microorganisms. A dissertation submitted to the department of genetics and the committee on graduate studies of Stanford University in partial fulfillment of the requirements for the degree of doctor of philosophy, Mar. 2010, pp. i, ii and 10-30.*
Kirby, J.R. In vivo mutagenesis using EZ-Tn5TM. Methods in Enzymology, vol. 421, pp. 17-21, 2007.*
Shevchenko et al. Systematic sequencing of cDNA clones using the transposon Tn5. Nucleic Acids Research, vol. 30, No. 11, pp. 2469-2477, 2002.*
Zeevi et al. Increasing cloning possibilities using artificial zinc finger nucleases. Proceedings of the National Academy of Sciences, USA, vol. 105, No. 35, pp. 12785-12790, Sep. 2008.*
Goodman et al. Identifying genetic determinants needed to establish a human gut symbiont in its habitat. Cell Host & Microbe, vol. 6, pp. 279-289, Sep. 2009.*
Heredia et al. In vitro double transposition for DNA identification. Analytical Biochemistry, vol. 399, pp. 78-83, Nov. 26, 2009.*
Adey, "Rapid, low-input, low-bias construction of shotgun fragment libraries by high-density in vitro transposition", Genome Biology 11 r119, Dec. 8, 2010, 47 pages.
Goryshin, et al., "Tn5 in Vitro Transposition", vol. 273, No. 13, Issue of Mar. 27, 1998, 7367-7374.
McCloskey, et al., "Encoding PCR Products with Batch-stamps and Barcodes", Biochem Genet 45:761, Jan. 31, 2007, 6 pages.
Miner, et al., "Molecular barcodes detect redundancy and contamination in hairpin-bisulfite PCR", Nucleic Acids Research, 2004, vol. 32, No. 17, Sep. 30, 2004, e135, 4 pages.
Savilahti, et al., "The Phage Mu transpososome core: DNA requirements for assembly and function", EMBO J., 14, 1995, 4893-4903.
Shendure, "Sequence Tag Directed Subassembly of Short Sequencing Reads Into Long Sequencing Reads", U.S. Appl. No. 61/096,720, filed Sep. 12, 2008.
International Search Report and Written Opinion, issued for PCT/US2011/059642, Apr. 10, 2012, 12 pages.
Benjamin, Bimber N. et al., "Whole-genome characterization of human and simian immunodeficiency virus intrahost diversity by ultradeep pyrosequencing", Journal of Virology, vol. 84, No. 22, Sep. 15, 2010, 12087-12092.
Fraz, Syed et al., "Optimized library preparation method for next-generation sequencing", Nature Methods, vol. 6, No. 10, Oct. 2009, I-II.
Haoyi, Wang et al., "Calling cards enable multiplexed identification of the genomic targets of DNA-binding proteins", Genome Research, vol. 21, No. 5, May 2011, 748-755.

(Continued)

*Primary Examiner* — Jennifer Dunston
(74) *Attorney, Agent, or Firm* — Kajal Chowdhury

(57) ABSTRACT

Artificial transposon sequences having code tags and target nucleic acids containing such sequences. Methods for making artificial transposons and for using their properties to analyze target nucleic acids.

22 Claims, 15 Drawing Sheets

(56) References Cited

OTHER PUBLICATIONS

Rachel, Marine et al., "Evaluation of a transposase protocol for rapid generation of shotgun high-throughput sequencing libraries from nanogram quantities of DNA", Applied and Environmental Microbiology, vol. 77, No. 22, Nov. 2011, 8071-8079.

Office Action issued for U.S. Appl. No. 12/559,124 on Mar. 27, 2012, 13 pages.

Kitzman, et al., "Hapiotype-resolved genome sequencing of a Gujarati Indian individual", Nature Biotechnology, vol. 29(1), Jan. 2011, 59-63.

Nijman, et al., "Mutation discovery by targeted genomic enrichment of multiplexed barcoded samples", Nature Methods, vol. 7, No. 11, Nov. 2010, 913-915.

Syed, "Next-generation sequencing library preparation: simultaneous fragmentation and tagging using in vitro transposition", Application Notes, Nature Methods, Epicentre Biotech, Nov. 2009, i-ii.

Marine, et al. "Evaluation of a transposase protocol for rapid generation of shotgun high-throughput sequencing libraries from nanogram quantities of DNA", Appl. Environ. Microbiol, vol. 77 (22), Nov. 2011, pp. 8071-8079.

Bloch, et al., "Purification of *Escherichia coli* chromosomal segments without cloning", Biochemical and Biophysical Research Communications, vol. 223, 1996, 104-111.

Gal, et al., "Directional cloning of native PCR products with preformed sticky ends (autosticky PCR)", Molecular & General Genetics, vol. 260, No. 6, Jan. 1999, 569-573.

Pobigaylo, et al., "Construction of a large signature-tagged miniTn5 transposon library and its application to mutagenesis of *Sinorhizobium meliloti*", Applied and Environmental Microbiology, vol. 72, No. 6, Jun. 2006, 4329-4337.

Zhou, et al., "Molecular genetic analysis of transposase—end DNA sequence recognition: Cooperatively of three adjacent base-pairs in specific interaction with a mutant Tn5 transposase", Journal of Molecular Biology, vol. 276, 1998, 913-925.

"GS FLX Titanium LV emPCR Kit (Lib-L) protocol", Aug. 2008, 1-2.

Ball, et al., "Targeted and genome-scale strategies reveal gene-body methylation signatures in human cells", Nat Biotechnol 27(4), 2009, 361-368.

Bansal, et al., "An efficient and accurate algorithm for the haplotype assembly problem", Bioinformatics;24(16), 2008, i153-9.

Benetti, et al., "A mammalian microRNA cluster controls DNA methylation and telomere recombination via Rbl2-dependent regulation of DNA methyltransferases.", Nat Struct Mol Bioi 15(3), 2008, 268-279.

Bentley, et al., "Accurate whole human genome sequencing using reversible terminator chemistry", Nature, vol. 456, No. 7218, Nov. 6, 2008, 53-59.

Branton, et al., "The potential and challenges of nanopore sequencing", Nature Biotechnology, vol. 26, No. 10, Oct. 2008, 1146-1153.

Braslavsky, et al., "Sequence information can be obtained from single DNA molecules", PNAS, 100(7), 2003, 3960-3964.

Clark, et al., "High sensitivity mapping of methylated cytosines", Nucleic Acids Research, vol. 22, No. 15, 1994, 2990-2997.

Cokus, et al., "Shotgun bisulphite sequencing of the *Arabidopsis* genome reveals DNA methylation patterning" Nature 452.7184, 2008, 215-219.

Deng, et al., "Targeted bisulfite sequencing reveals changes in DNA methylation associated with nuclear reprogramming.", Nat Biotechnol 27(4), 2009, 353-360.

Down, et al., "A Bayesian deconvolution strategy for immunoprecipitation-based DNA methylome analysis.", Nat Biotechnol 26(7), 2008, 779-785.

Dressman, et al., "Transforming single DNA molecules into fluorescent magnetic particles for detection and enumeration of genetic variations", PNAS, 100(15), 2003, 8817-8822.

Drmanac, et al., "Human genome sequencing using unchained base reads on self-assembling DNA nanoarrays", Science.2009; 327(5961), 2009, 78-81.

Duan, et al., "A three-dimensional model of the yeast genome", Nature; 465(7296), 2010, 363-7.

Eid, J. et al., "Real-Time DNA Sequencing from Single Polymerase Molecules", Science 323,, 2009, 133-138.

Fan, et al., "Whole-genome molecular haplotyping of single cells.", Nat Biotech 29(1):, 2011, 51-57.

Fullwood, et al., "An oestrogen-receptor-_-bound human chromatin interactome", Nature 462, 2009, 58-64.

Geiss, et al., "Direct multiplexed measurement of gene expression with colorcoded probe pairs", Nat Biotechnol.; 26(3), 2008, 317-25.

Gnerre, et al., "High-quality draft assemblies of mammalian genomes from massively parallel sequence data", Proc Natl Acad Sci USA., [Epub ahead of print] PubMed PMID: 21187386, Dec. 27, 2010.

Gu, et al., "Preparation of reduced representation bisulfite sequencing libraries for 'genome-scale DNA methylation profiling", Nat Protoc 6(4), 2011, 468-481.

Harris, et al., "Comparison of sequencing-based methods to profile DNA methylation and identification of monoallelic epigenetic modifications.", Nat Biotechnol 28(10), 2010, 1097-1105.

Hiatt, et al., Tag-directed assembly of locally derived short sequence reads, Nat Methods. 7(2), 2010, 119-22.

Johnson, et al., "Genome-wide mapping of in vivo protein-DNA interactions", Science. 316(5830)., 2007, 1497-502.

Kidd, et al., "Mapping and sequencing of structural variation from eight human genomes", Nature. 453 (7191), 2008, 56-64.

Lai et al., "A shotgun optical map of the entire *Plasmodium falciparum* genome," Nat Genet. 23(3), 1999, 309-13.

Lander, et al., "Initial sequencing and analysis of the human genome", Nature, 409(6822), 2001, 860-921.

Levy, et al., "The Diploid Genome Sequence of an Individual Human", PLoS Biology, vol. 5, Issue 10, Oct. 2007, 2113-2144.

Li, et al., "Fast and accurate short read alignment with Burrows-Wheeler transform", Bioinformatics 25:1754-1760, 2009.

Li, et al., "De novo assembly of human genomes with massively parallel short read sequencing", Genome Res. 20 (2), 2010, 265-72.

Li, et al., "Primasebased whole genome amplification", Nucleic Acids Res. 36(13), 2008, e79.

Li, et al., "The DNA methylome of human peripheral blood mononuclear cells", PLoS Biol 8(11), 2010, e1000533.

Lieberman-Aiden, et al., "Comprehensive mapping of long-range interactions reveals folding principles of the human genome", Science. 326(5950), 2009, 289-93.

Lim, et al., "Shotgun optical maps of the whole *Escherichia coli* 0157:H7 genome", Genome Res. 11(9), 2001, 1584-93.

Lin, et al., "Wholegenome shotgun optical mapping of *Deinococcus radiodurans*.", Science. 285(5433):, 1999, 1558-62.

Lister, et al., "Human DNA methylomes at base resolution show widespread epigenomic differences", Nature, 462(7271), Nov. 19, 2009, 315-322.

Margulies, et al., "Genome sequencing in microfabricated high-density picolitre reactors", Nature, 437, Correction: Nature 441, 120, 2005, 376-380.

Mazutis, et al., "Droplet-based microfluidic systems for high-throughput single DNA molecule isothermal amplification and analysis", Anal Chem. 81 (12), 2009, 4813-21.

Meissner, et al., Nucleic Acids Research, 33, 2005, 5868-5877.

Mitra, Robi D., et al., "Fluorescent in situ sequencing on polymerase colonies", Analytical Biochemistry—320 (2003) 55-65, 2003, 55-65.

Mortazavi, Ali, et al., "Mapping and quantifying mammalian transcriptomes by RNA-seq", Nature Methods, 5(7), 2008, 621-8.

Ng, et al., "Targeted capture and massively parallel sequencing of 12 human exomes", Nature. 461 (7261), 2009, 272-6.

Ramanathan, et al., "An integrative approach for the optical sequencing of single DNA molecules", Analytical Biochemistry, vol. 330, No. 2, 2004, 227-241.

Riehn et al., "Restriction mapping in nanofluidic devices.", Proceedings of the National Academy of Sciences of the United States of America 102(29):, 2005, 10012-10016.

Ritz, et al., "Structural variation analysis with strobe reads", Bioinformatics. 26(10), 2010, 1291-8.

(56) References Cited

OTHER PUBLICATIONS

Shendure, et al., "Accurate Multiplex Polony Sequencing of an Evolved Bacterial Genome", Science, vol. 309, Sep. 9, 2005, 1728-1732.
Shendure, et al., "Advanced sequencing technologies: methods and goals", Nature Rev. Genet., 5, 2004, 335-344.
Shendure, et al., "Next-generation DNA sequencing", Nature Biotechnology 26(10), 2008, 1135-1145.
Steensel et al., "Genomics tools for unraveling chromosome architecture", Nature Bitoechnology, Oct. 13, 2010.
Syed, Fraz, et al., "Optimized library preparation method for next-generation sequencing", Nature Methods, 6(10), 2009, I-II.
Van Berkum, et al., "Method to Study the Three-dimensional Architecture of Genomes", http://www.jove.com/details.stp?id=1869 doi:10.3791/1869. J Vis Exp.39, (2010).
Waterston, et al., "Initial sequencing and comparative analysis of the mouse genome", Nature. 420(6915), 2002, 520-62.
Waterston, et al., "On the sequencing of the human genome", Pro Proc Natl Acad Sci USA. 99(6), 2002, 3712-6.
Zeng, et al., "High-performance single cell genetic analysis using microfluidic emulsion generator arrays.", Anal Chern. 82 (8), 2010, 3183-90.
Zhou, et al., "A Single Molecule Scaffold for the Maize Genome", PLoS Genet 5(11), 2009, e1000711.
Zhou, et al., "Validation of rice genome sequence by optical mapping", BMC Genomics 8(1), 2007, 278.
Zilberman, et al., Genome-wide analysis of DNA methylation patterns., Development 134(22), 2007, 3959-3965.
Brownlie, et al., "The *Caenorhabditis briggsae* genome contains active CbmaT1 and Tcb1 transposons," Molecular Genetics and Genomics, vol. 273, 2005, 92-101.
Keith, et al., "Algorithms for Sequence Analysis via Mutagenesis," Bioinformatics, vol. 20 No. 15; published online doi:10.1093/bioinformatics/bth258, May 14, 2004, 2401-2410.
Keith, et al., "Unlocking Hidden Genomic Sequence," Nucleic Acids Research, vol. 32, No. 3, published online DOI: 10.1093/nar/gnh022, Feb. 18, 2004, e35.
Ooka, et al., "Inference of the impact of insertion sequence (IS) elements on bacterial genome diversification through analysis of small-size structural polymorphisms in *Escherichia coli* O157 genomes," Genome Research, vol. 19, 2009, 1809-1816.
Sipos, et al., "An Improved Protocol for Sequencing of Repetitive Genomic Regions and Structural Variations Using Mutagenesis and Next Generation Sequencing," PLoS One 7(8), published online doi:10.1371/journal.pone.0043359, Aug. 17, 2012, e43359.
Fullwood, Melissa J. et al., "Chromatin interaction analysis using paired-end tag sequencing", Current Protocols in Molecular Biology, Supplement 89, Jan. 21, 2010, 21.15.1-21.15.25.
Grunenwald, et al., "Rapid, high-throughput library preparation for next-generation sequencing, Nature Methods, Application Notes", Aug. 2010, iii-iv.
EPO communication pursuant to Article 94(c) EPC, mailed Oct. 28, 2014, for Application No. 11802179.9.
International Search Report and Written Opinion for PCT/US12/23679, Applicant: University of Washington Through Its Center for Commercialization, Date of Mailing: Aug. 24, 2012.
Supplementary European Search Report for Application EP12741945.5, Applicant: University of Washington Through Its Center for Commercialization, Date of Mailing: Sep. 22, 2014.
Adey et al., "Rapid, low-input, low-bias construction of shotgun fragment libraries by high-density in vitro transposition", Genome Biology vol. 11(12), 2010, R119.
Caruccio et al., "Preparation of next-generation sequencing libraries using Nextera$^{TM}$ technology: simultaneous DNA fragmentation and adaptor tagging by in vitro transposition", Methods in Molecular Biology, 733, Jan. 1, 2011, 241255.
Schwartz et al., "Capturing native long-range contiguity by in situ library construction and optical sequencing", PNAS, vol. 109m No. 46, 2012, 18749-18754.

\* cited by examiner

Exemplary linkers:

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Primer Sequence

<400> SEQUENCE: 1
agatgtgtat aagagacag                                                  19

<210> SEQ ID NO 2
<211> LENGTH: 19
<212> TYPE: DNA
<213> ORGANISM: Artificial Sequence
<220> FEATURE:
<223> OTHER INFORMATION: Primer Sequence

<400> SEQUENCE: 2
ctgtctctta tacacatct                                                  19

<210> SEQ ID NO 3
<211> LENGTH: 10
<212> TYPE: PRT
<213> ORGANISM: Artificial Sequence
<220> FEATURE:
<223> OTHER INFORMATION: c-MYC epitope

<400> SEQUENCE: 3

Glu Gln Lys Leu Ile Ser Glu Glu Asp Leu
 1               5                  10

<210> SEQ ID NO 4
<211> LENGTH: 9
<212> TYPE: PRT
<213> ORGANISM: Artificial Sequence
<220> FEATURE:
<223> OTHER INFORMATION: HA epitope

<400> SEQUENCE: 4

Tyr Pro Tyr Asp Val Pro Asp Tyr Ala
 1               5
```

```
<210> SEQ ID NO 5
<211> LENGTH: 11
<212> TYPE: PRT
<213> ORGANISM: Artificial Sequence
<220> FEATURE:
<223> OTHER INFORMATION: VSV-G epitope

<400> SEQUENCE: 5

Tyr Thr Asp Ile Glu Met Asn Arg Leu Gly Lys
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: HSV epitope

<400> SEQUENCE: 6

Gln Pro Glu Leu Ala Pro Glu Asp Pro Glu Asp
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: V5 epitope

<400> SEQUENCE: 7

Gly Lys Pro Ile Pro Asn Pro Leu Leu Gly Leu Asp Ser Thr
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: FLAG Tag(TM) epitope

<400> SEQUENCE: 8

Asp Tyr Lys Asp Asp Asp Asp Lys Gly
 1               5
```

LINKING SEQUENCE READS USING PAIRED CODE TAGS

RELATED APPLICATIONS

This application is a continuation-in-part of U.S. application Ser. No. 13/025,022, filed Feb. 10, 2011 entitled "LINKING SEQUENCE READS USING PAIRED CODE TAGS," now U.S. Pat. No. 8,829,171, the contents of which are incorporated herein by reference in its entirety.

REFERENCE TO SEQUENCE LISTING

The present application is being filed along with a Sequence Listing in electronic format. The Sequence Listing is provided as a file entitled ILLINC193P1SEQLIST.TXT, created Mar. 30, 2011, which is approximately 2 Kb in size. The information in the electronic format of the Sequence Listing is incorporated herein by reference in its entirety.

FIELD OF THE INVENTION

Embodiments of the present invention relate to the fields of biology and genomics. Some embodiments of the present invention relate to methods and compositions that include certain transposon sequences. Some such methods and compositions include analyzing target nucleic acids.

BACKGROUND OF THE INVENTION

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of nucleic acids all in a single sequencing run. As such, the information generated from a single sequencing run can be enormous.

SUMMARY OF THE INVENTION

Some embodiments of the present invention relate to methods and compositions that include certain transposon sequences. Some such methods and compositions include analyzing target nucleic acids. Some embodiments include methods of preparing a template nucleic acid. Some such methods include: (a) providing a target nucleic acid; (b) providing a plurality of transposon sequences, each transposon sequence comprising a first transposase recognition site, a second transposase recognition site having a barcode disposed therebetween; and (c) contacting the target nucleic acid with the plurality of transposon sequences under conditions such that at least a portion of said plurality of transposon sequences inserts into the target nucleic acid, thereby preparing a template nucleic acid.

In some embodiments, the barcode of each transposon is different.

In some embodiments, the barcode comprises a first barcode sequence, a second barcode sequence, said first and second barcode sequences being separated by a linker disposed therebetween.

In some embodiments, the barcode comprises a double-stranded nucleic acid sequence comprising a first strand barcode and a second strand barcode. In some embodiments, the first strand barcode and second strand barcode comprise complementary sequences. In some embodiments, the first strand barcode and second strand barcode comprise non-complementary sequences.

In some embodiments, the linker comprises a nucleic acid.

In some embodiments, the linker comprises a sequencing adapter comprising a first primer site.

In some embodiments, the linker comprises a fragmentation site. In some embodiments, the fragmentation site comprises a first nickase recognition sequence and a second nickase recognition sequence, wherein the cut site for each recognition sequence is the same site. In some embodiments, the fragmentation site comprises a restriction endonuclease recognition sequence.

In some embodiments, the linker comprises a sequencing adapter comprising a first primer site and a fragmentation site. In some embodiments, the linker comprises a sequencing adapter comprising a first primer site and a second primer site having a fragmentation site disposed therebetween.

Some embodiments include methods of preparing a library of template nucleic acids. Some such methods include: (a) providing a target nucleic acid; (b) providing a plurality of transposon sequences, each transposon sequence comprising a first transposase recognition site and a second transposase recognition site having a barcode disposed therebetween, wherein the barcode comprises a first barcode sequence and a second barcode sequence being separated by a sequencing adapter disposed therebetween, wherein the sequencing adapter comprises a first primer site and a second primer site; and (c) contacting the target nucleic acid with the plurality of transposon sequences under conditions such that at least a portion of said plurality of transposon sequences inserts into the target nucleic acid; and (d) amplifying at least a portion of the target nucleic acid by hybridizing a primer to said first primer site and a primer to said second primer site, such that the amplification product comprises a first barcode sequence and a second barcode sequence, thereby preparing a library of template nucleic acids.

In some embodiments, the barcode of each transposon is different.

Some methods also include a step subsequent to (c) and prior to (d) comprising reducing the number of target nucleic acid molecules comprising inserted transposon sequences.

In some embodiments, the sequencing adapter comprises a first primer site, a second primer site, and a non-amplifiable site therebetween. In some embodiments, the non-amplifiable site comprises a nucleic acid. In some embodiments, the non-amplifiable site comprises at least one nucleotide analogue. In some embodiments, the nucleotide analogue does not significantly basepair with A, C, G or T.

Some embodiments include methods of preparing a library of template nucleic acids. Some such methods include: (a) providing a target nucleic acid; (b) providing a plurality of transposon sequences, each transposon sequence comprising a first transposase recognition site and a second transposase recognition site having a barcode disposed therebetween, wherein the barcode comprises a first barcode sequence and a second barcode sequence being separated by a linker disposed therebetween, wherein the linker comprises a fragmentation site; (c) contacting the target nucleic acid with the plurality of transposon sequences under conditions such that at least a portion of said plurality of transposon sequences inserts into the target nucleic acid; and (d) fragmenting said target nucleic acid at said fragmentation sites, such that at least a portion of the fragmented nucleic acids each comprise a first barcode sequence and a second barcode sequence, thereby preparing a library of template nucleic acids.

In some embodiments, the barcode of each transposon is different.

In some embodiments, the linker comprises a nucleic acid.

In some embodiments, the fragmentation site comprises a first nickase recognition sequence, a second nickase recognition sequence, wherein the cut site for each recognition sequence is the same site.

In some embodiments, the fragmentation site comprises a restriction endonuclease recognition sequence.

In some methods, the fragmenting comprises contacting the target nucleic acid with a polymerase. Useful polymerases include those with exonuclease activity (such as 3' to 5' activity, e.g., E. coli DNA polymerase III, or 5' to 3' activity, e.g., E. coli DNA polymerase I), non-strand-displacing (e.g. T4 DNA polymerase) and strand-displacing activities (e.g. Bst DNA polymerase, large fragment).

Some methods also include ligating a first primer site to a first end of at least one fragmented nucleic acid. Some methods also include ligating a second primer site to the second end of the at least one fragmented nucleic acid.

Some methods also include amplifying said at least one fragmented nucleic acid by hybridizing a primer to the first primer site and a primer to the second primer site.

In some embodiments, the linker further comprises a first primer site.

In some embodiments, the linker comprises a sequencing adapter comprises a first primer site, a second primer site having the fragmentation site disposed therebetween. Some methods also include amplifying said at least a portion of the fragmented nucleic acids by hybridizing a primer to said first primer site and a primer to said second primer site.

In some embodiments, the target nucleic acid comprises genomic DNA.

In some embodiments, the first transposase recognition site comprises a mosaic element.

In some embodiments, the sequences of the first barcode and the second barcode comprise the reverse complements of each other.

Some embodiments include libraries of template nucleic acids prepared by any one of the foregoing methods.

Some embodiments include methods of preparing a transposon sequence. Some such methods include: (a) providing a transposon template nucleic acid sequence comprising a first transposase recognition site, a first barcode 3' thereof, and a linker 3' thereof; and (b) extending the transposon template sequence by hair-pin extension, such that the extended transposon template sequence further comprises sequences complementary to said barcode and to said transposase recognition site, thereby preparing a transposon comprising a first transposase recognition site, a first barcode, a linker, a second barcode, and a second transposase recognition site.

In some embodiments, the barcode comprises a random sequence.

In some embodiments, the transposase recognition site comprises a mosaic element.

In some embodiments, the barcode comprises at least about five nucleotides.

In some embodiments, the linker comprises a nucleic acid.

In some embodiments, the linker comprises a fragmentation site. In some embodiments, the fragmentation site comprises a first nickase recognition sequence, a second nickase recognition sequence, wherein the cut site for each recognition sequence is the same site. In some embodiments, the fragmentation site comprises a restriction endonuclease recognition sequence.

In some embodiments, the linker comprises a sequencing adapter. In some embodiments, a sequencing adapter comprises a first primer site and second primer site. In some embodiments, the sequencing adapter comprises a first primer site and a second primer site having a fragmentation site disposed therebetween. In some embodiments, the sequencing adapter comprises a first primer site and a second primer site, having a non-amplifiable site disposed therebetween.

In some embodiments, the non-amplifiable site comprises a nucleic acid. In some embodiments, the non-amplifiable site comprises at least one nucleotide analogue. In some embodiments, the nucleotide analogue does not significantly base-pair with A, C, G or T.

Some embodiments include methods of preparing a plurality of transposon sequences. Some such method include repeating steps (a) and (b) of any one of the foregoing methods of preparing a transposon sequence, wherein the barcode of each transposon template nucleic acid is different.

Some embodiments include transposons prepared by the method of any one of the foregoing methods of preparing a transposon sequence.

Some embodiments include methods of analyzing a target nucleic acid. Some such methods include: (a) providing a template nucleic acid, wherein the template nucleic acid comprises the target nucleic acid and a plurality of markers inserted therein, wherein each marker sequence comprises a barcode comprising a first barcode sequence and a second barcode sequence, having a sequencing adapter disposed therebetween, wherein the sequencing adapter comprises a first primer site; (b) obtaining sequence data from said template nucleic acid; and (c) assembling a representation of at least a portion of said target nucleic acid from said sequence data.

In some embodiments, the barcode of each marker is different.

In some embodiments, the barcode comprises a double-stranded nucleic acid sequence comprising a first strand barcode and a second strand barcode. In some embodiments, the first strand barcode and second strand barcode comprise complementary sequences. In some embodiments, the first strand barcode and second strand barcode comprise non-complementary sequences.

In some embodiments, obtaining sequence data comprises hybridizing a primer to said first primer site, and extending said primer.

In some embodiments, the sequencing adapter comprises a second primer site, and said obtaining sequence data comprises hybridizing a primer to the second primer site and extending said primer. In some embodiments, the primers hybridize to the sites in opposite orientations.

In some embodiments, the sequences of the first barcode sequence and the second barcode sequence comprise the reverse complements of each other.

In some embodiments, the assembling step comprises identifying more than one sequencing read comprising the first barcode sequence or second barcode sequence of a barcode.

In some embodiments, the presence of a first barcode sequence or second barcode sequence of a barcode in more than one sequencing read is indicative of the more than one sequencing reads representing sequences adjacent to each other in the target nucleic acid.

In some embodiments, each marker sequence comprises a first host tag and second host tag having the barcode disposed therebetween. In some embodiments, the first and second host tag of a marker comprises the same sequence. In some embodiments, the assembling step further comprises identifying more than one sequencing read comprising the same host tags.

In some embodiments, the target nucleic acid comprises genomic DNA.

Other embodiments include artificial transposon sequences. Some such artificial transposon sequences include: a first transposase recognition site and a second transposase recognition site having a barcode disposed therebetween, wherein the barcode comprises a first barcode sequence and a second barcode sequence, said first and second barcode sequences being separated by a linker.

In some embodiments, the barcode comprises a double-stranded nucleic acid sequence comprising a first strand barcode and a second strand barcode. In some embodiments, the first strand barcode and second strand barcode comprise complementary sequences. In some embodiments, the first strand barcode and second strand barcode comprise non-complementary sequences.

In some embodiments, the first transposon recognition site comprises a mosaic element.

In some embodiments, the linker comprises a nucleic acid.

In some embodiments, the linker comprises a fragmentation site. In some embodiments, the fragmentation site comprises a first nickase recognition sequence and a second nickase recognition sequence, wherein the cut site for each recognition sequence is the same site. In some embodiments, the fragmentation site comprises a restriction endonuclease recognition sequence.

In some embodiments, the linker comprises a sequencing adapter comprising a first primer site. In some embodiments, the sequencing adapter comprises a second primer site. In some embodiments, the sequencing adapter comprises a first primer site and a second primer site, having a non-amplifiable site disposed therebetween. In some embodiments, the non-amplifiable site comprises a nucleic acid. In some embodiments, the non-amplifiable site comprises at least one nucleotide analogue. In some embodiments, the nucleotide analogue does not significantly basepair with A, C, G or T.

In some embodiments, the linker comprises a sequencing adapter comprising a first primer site and a second primer site, having a fragmentation site disposed therebetween.

In some embodiments, a sequencing primer is hybridized to said first primer site.

In some embodiments, a sequencing primer is hybridized to said first transposase recognition site.

Some embodiments include populations of artificial transposon sequences comprising a plurality of any one of the foregoing artificial transposon sequences.

Some embodiments include target nucleic acids or copies thereof having a population of the artificial transposon sequences integrated therein, wherein the artificial transposon sequences comprise any one of the artificial transposon sequences described herein.

Some embodiments include populations of genomic DNA fragments or copies thereof having a population of the artificial transposon sequences integrated therein, wherein the artificial transposon sequences comprise any one of the artificial transposon sequences described herein.

Some embodiments include genomes having a population of artificial transposon sequences integrated therein, wherein the artificial transposon sequences comprise any one of the artificial transposon sequences described herein.

Some embodiments include isolated template nucleic acids. Some such isolated template nucleic acids include at least a portion of a target nucleic acid or copy thereof and at least two markers inserted therein, wherein each marker sequence comprises a barcode.

In some embodiments, the barcode of each marker is different.

In some embodiments, the barcode comprises a double-stranded nucleic acid sequence comprising a first strand barcode and a second strand barcode. In some embodiments, the first strand barcode and second strand barcode comprise complementary sequences. In some embodiments, the first strand barcode and second strand barcode comprise non-complementary sequences.

Some embodiments also include a transposase recognition site.

Some embodiments also include a first transposase recognition site and a second transposes recognition site, having the at least a portion of a target nucleic acid or copy thereof disposed therebetween.

Some embodiments also include a host tag. Some embodiments also include a first host tag and a second host tag, having the at least a portion of a target nucleic acid or copy thereof disposed therebetween. Some embodiments also include a first host tag and a second host tag, having a transposase recognition site disposed therebetween, wherein the transposase recognition site comprises a first transposase recognition site and a second transposase recognition site, having the at least a portion of a target nucleic acid or copy thereof disposed therebetween.

In some embodiments, the host tag comprises nine nucleotides.

In some embodiments, the target nucleic acid comprises genomic DNA.

Some embodiments include a plurality of template nucleic acids comprising the template nucleic acid of any one of the isolated template nucleic acids described herein, wherein a first template nucleic acid of said plurality comprises a first barcode, and a second template nucleic acid comprises a second barcode, wherein the first and second barcodes are indicative of template nucleic acid sequences being adjacent to one another in a sequence representation of the target nucleic acid. In some embodiments, the first barcode comprises the reverse complement sequence of the second barcode.

Some embodiments include substrates comprising nucleotide sequences attached thereto, at least one of said nucleotide sequences comprising any one of the template nucleic acids described herein, or any one of the plurality of template nucleic acids described herein. In some embodiments, the substrate can include a solid support selected from the group consisting of spheres, microparticles, beads, membranes, slides, plates, micromachined chips, tubes, microwells, microfluidic devices, channels, and filters.

Some embodiments include artificial transposons comprising: a first transposase recognition site, a second transposase recognition site, and a barcode disposed therebetween, wherein the barcode comprises a double-stranded nucleic acid sequence comprising a first strand barcode and a second strand barcode.

In some embodiments, the first transposase recognition site comprises a hyperactive Tn5 transposase recognition site.

In some embodiments, the first transposase recognition site comprises a Mu transposase recognition site.

In some embodiments, the first transposase recognition site comprises an IS5 transposase recognition site or an IS911 transposase recognition site.

In some embodiments, the transposon is associated with an affinity tag.

In some embodiments, the affinity tag is associated with a protein that targets specific nucleic acid sequences.

In some embodiments, the first strand barcode and the second strand barcode comprise complementary sequences.

In some embodiments, the first strand barcode and the second strand barcode comprise non-complementary sequences.

In some embodiments, a transposon further comprises at least one universal primer site.

Some embodiments include isolated template nucleic acids comprising at least a portion of a target nucleic acid or copy thereof and at least a first transposon and second transposon provided herein, wherein the barcode of the first transposon is different from the barcode of the second transposon.

Some embodiments include methods for preparing a library of template nucleic acids comprising: (a) contacting a target nucleic acid with a plurality of transposons of claim 1 under conditions such that a portion of said of transposons are inserted into the target nucleic acid; and (b) fragmenting said target nucleic acid.

In some embodiments, the target nucleic acid comprises cDNAs from a single cell.

In some embodiments, the target nucleic acid comprises nucleic acids from a plurality of species.

In some embodiments, the target nucleic acid comprises nucleic acids from a plurality of haplotypes.

In some embodiments, the fragmentation comprises contacting the target nucleic acid with a polymerase.

In some embodiments, the polymerase has 3' to 5' exonuclease activity.

Some embodiments include methods for preparing a library of template nucleic acids, comprising: (a) contacting a target nucleic acid with a plurality of transposons of claim 1, further comprising a first primer site, under conditions such that a portion of said transposons are inserted into the target nucleic acid; (b) hybridizing a primer to the first primer site; and (c) amplifying a portion of the transposon sequence.

Some embodiments include methods of analyzing a target nucleic acid comprising: (a) contacting a target nucleic acid with a plurality of transposons of claim 1, further comprising a first primer site, under conditions such that a portion of said transposons are inserted into the target nucleic acid; (b) hybridizing a primer to the first primer site; (c) amplifying a portion of the transposon sequence; (d) obtaining sequence data from said templates; and (e) assembling a representation of a portion of said target nucleic acid from said sequence data.

In some embodiments, step (e) comprises identifying the presence of a first barcode in one sequencing read and the presence of a corresponding barcode in another sequencing read, thereby indicating proximity between the two sequencing reads in the target nucleic acid.

In some embodiments, step (d) is terminated after the barcode is identified.

BRIEF DESCRIPTION OF THE DRAWINGS

FIG. 1 also depicts exemplary linker sequences. For example, linker sequences can have fragmentation sites, such as those with nickase recognition sites (e.g. N1, N2) or a restriction endonuclease recognition sequence (indicated by RE). In other embodiments, linkers can contain one or more primer sites (e.g. A, B), corresponding to complementary primers A' and B'. A non-amplifiable site is indicated by nA.

DETAILED DESCRIPTION

Figure 1A:
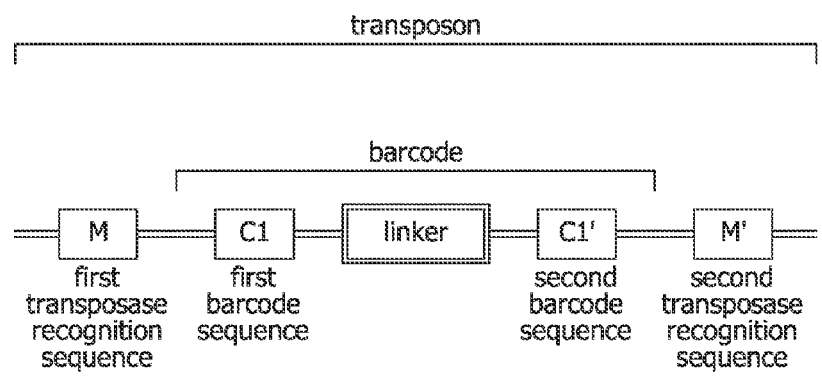
FIG. 1A depicts a schematic a transposon sequence. M indicates a first transposon recognition sequence. C1 indicates a first barcode sequence. The linker sequence is indicated by a rectangle with a double border. C1' indicates a second barcode sequence. M' indicates a second transposase recognition sequence.
Figure 1A:
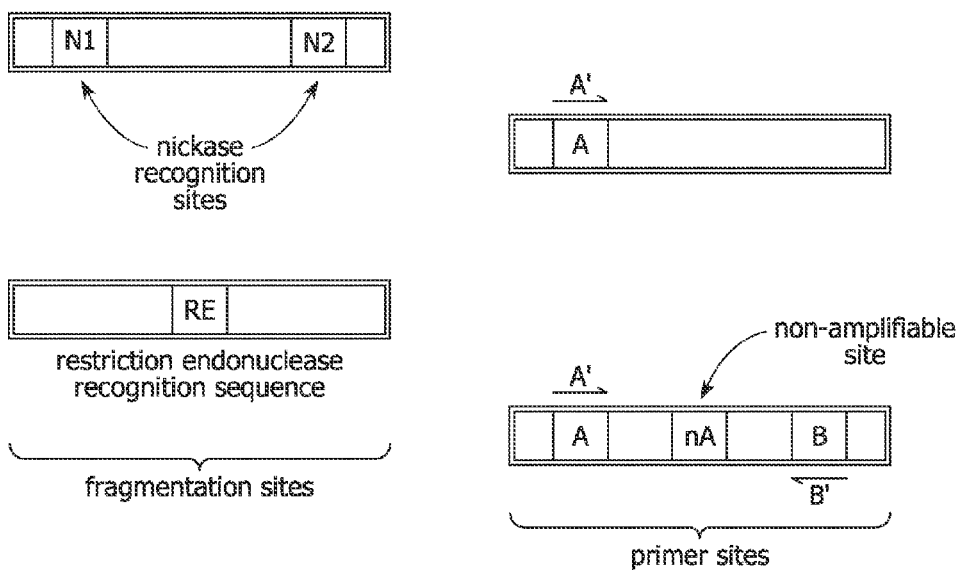

Some embodiments of the present invention relate to methods and compositions that include certain transposon sequences. Some such methods and compositions include analyzing target nucleic acids. Generally, methods of analyzing nucleic acids include preparing a library of template nucleic acids of a target nucleic acid, obtaining sequence data from the library of template nucleic acids, and assembling a sequence representation of the target nucleic acid from such sequence data. However, assembly of a sequence representation using traditional methods is met with several challenges. For example, sequencing data is obtained using short reads and thus there is difficulty assembling contiguous reads through repetitive sequences of a target nucleic acid. In addition, many contigs are required to be constructed to represent a genome such as the human genome. Methods such as paired-end sequencing can be used to mitigate the difficulties of assembling sequence data from many short reads. However, the paired-end sequencing methods require longer template nucleic acids to span repetitive sequences in a target nucleic acid; preparation of template nucleic acids is inefficient and thus requires larger amounts of DNA; the number of different paired-ends is limited; and a reference genome is required to verify any resulting sequence representation.

Some nucleic acids of interest, such as genomic DNAs, comprise long molecules with ordered sequence. Methods to sequence such molecules tend to be highly parallelized and include sequencing short libraries in order to create high throughput. Consequently, such methods require assembly of the shorter reads to obtain ordering information, i.e., a sequence representation of the target nucleic acid. Shotgun sequencing approaches uses DNA fragmentation; however, order information is lost during fragmentation. Advantageously, some methods and compositions provided herein can be used to obtain shorter reads of template nucleic acids in which the order information is preserved. Thus, assembly of shorter reads can be performed without the requirement of a reference genome.

In an exemplary embodiment, a library of template nucleic acids is prepared from a target nucleic acid. The library is prepared by inserting a plurality of unique barcodes throughout the target nucleic acid.

As will be understood, although a barcode is frequently depicted in the figures as a double-stranded, annealed structure, a useful barcode can be a double-stranded region where the two strands are not complementary or not annealed. For example, two noncomplementary regions can be linked informatically, even though they are not complementary in a conventional Watson-Crick base-pairing.

Each barcode includes a first barcode sequence and a second barcode sequence, having a fragmentation site disposed therebetween. The first barcode sequence and second barcode sequences can be identified or designated to be paired with one another. The pairing can be informatic so that a first barcode is associated with a second barcode. The pairing can also be physically associated to form a junction between the two barcodes. For example, the first barcode sequence and second barcode sequences can be the tandem or reverse complements of each other. The target nucleic acid can be fragmented at the fragmentation sites, and a library of template nucleic acids can be prepared from the fragments. Sequencing information can be obtained from the library of template nucleic acids. Advantageously, the paired barcode sequences can be used to assemble sequencing data from the library of template nucleic acids. For example, identifying a first template nucleic acid comprising a first barcode sequence and a second template nucleic acid comprising a second barcode sequence that is paired with the first indicates that the first and second template nucleic acids represent sequences adjacent to one another in a sequence representation of the target nucleic acid. In essence, two sequences originally adjacent in the target nucleic acid may be separated from each other, introducing one barcode of a barcode pair at their points of separation, so that even when sequenced separately, the detection of the paired barcodes indicates the original proximity of the two sequences. Despite having been separated physically, they can be reunited bioinformatically, much as each divided half sought its other half in Plato's *Symposium*. Thus, a sequence representation of the target nucleic acid can be assembled by identifying further sequencing reads comprising paired barcode sequences. Such methods can be used to assemble a sequence representation of a target nucleic acid de novo, without the requirement of a reference genome. Moreover, such methods are also useful to sequence target nucleic acids comprising highly repetitive sequences. The methods can also be used to reassemble alternative isoforms and splice junctions in cDNAs, as well as reassemble single-molecule haplotypes.

DEFINITIONS

As used herein the term "nucleic acid" and/or "oligonucleotide" and/or grammatical equivalents thereof can refer to at least two nucleotide monomers linked together. A nucleic acid can generally contain phosphodiester bonds; however, in some embodiments, nucleic acid analogs may have other types of backbones, comprising, for example, phosphoramide (Beaucage, et al., Tetrahedron, 49:1925 (1993); Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986), incorporated by reference in their entireties), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989), incorporated by reference in its entirety), O-methylphosphoroamidite linkages (see Eckstein, Oligonucleotides and Analogues: A Practical Approach, Oxford University Press, incorporated by reference in its entirety), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), incorporated by reference in their entireties).

Other analog nucleic acids include those with positive backbones (Denpcy, et al., Proc. Natl. Acad. Sci. USA, 92:6097 (1995), incorporated by reference in its entirety); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996), incorporated by reference in their entireties) and non-ribose (U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Coo, incorporated by reference in their entireties). Nucleic acids may also contain one or more carbocyclic sugars (see Jenkins, et al., Chem. Soc. Rev., (1995) pp. 169 176).

Modifications of the ribose-phosphate backbone may be done to facilitate the addition of additional moieties such as labels, or to increase the stability of such molecules under certain conditions. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, for example, genomic or cDNA, RNA or a hybrid, from single cells, multiple cells, or from multiple species, as with metagenomic samples, such as from environmental samples. A nucleic acid can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc.

In some embodiments, a nucleic acid can include at least one promiscuous base. Promiscuous bases can base-pair with more than one different type of base. In some embodiments, a promiscuous base can base-pair with at least two different types of bases and no more than three different types of bases. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole (Loakes et al., Nucleic Acid Res. 22:4039 (1994); Van Aerschot et al., Nucleic Acid Res. 23:4363 (1995); Nichols et al., Nature 369:492 (1994); Bergstrom et al., Nucleic Acid Res. 25:1935 (1997); Loakes et al., Nucleic Acid Res. 23:2361 (1995); Loakes et al., J. Mol. Biol. 270:426 (1997); and Fotin et al., Nucleic Acid Res. 26:1515 (1998), incorporated by reference in their entireties). Promiscuous bases that can base-pair with at least three, four or more types of bases can also be used.

As used herein, the term "nucleotide analog" and/or grammatical equivalents thereof can refer to synthetic analogs having modified nucleotide base portions, modified pentose portions, and/or modified phosphate portions, and, in the case of polynucleotides, modified internucleotide linkages, as generally described elsewhere (e.g., Scheit, Nucleotide Analogs, John Wiley, New York, 1980; Englisch, Angew. Chem. Int. Ed. Engl. 30:613-29, 1991; Agarwal, Protocols for Polynucleotides and Analogs, Humana Press, 1994; and S. Verma and F. Eckstein, Ann. Rev. Biochem. 67:99-134, 1998). Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Example modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, 5-Me-Bz-C-LNA, dmf-G-LNA, and T-LNA (see, e.g., The Glen Report, 16(2):5, 2003; Koshkin et al., Tetrahedron 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., Organic Chem., 52:4202, 1987), and uncharged morpholino-based polymers having achiral intersubunit linkages (see, e.g., U.S. Pat. No. 5,034,506). Some internucleotide linkage analogs include morpholidate, acetal, and polyamide-linked heterocycles. In one class of nucleotide analogs, known as peptide nucleic acids, including pseudocomplementary peptide nucleic acids ("PNA"), a conventional sugar and internucleotide linkage has been replaced with a 2-aminoethylglycine amide backbone polymer (see, e.g., Nielsen et al., Science, 254:1497-1500, 1991; Egholm et al., J. Am. Chem. Soc., 114: 1895-1897 1992; Demidov et al., Proc. Natl. Acad. Sci. 99:5953-58, 2002; Peptide Nucleic Acids: Protocols and Applications, Nielsen, ed., Horizon Bioscience, 2004).

As used herein, the term "sequencing read" and/or grammatical equivalents thereof can refer to a repetitive process of physical or chemical steps that is carried out to obtain signals indicative of the order of monomers in a polymer. The signals can be indicative of an order of monomers at single monomer resolution or lower resolution. In particular embodiments, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. A sequencing read can be carried out on a single target nucleic acid molecule or simultaneously on a population of target nucleic acid molecules having the same sequence, or simultaneously on a population of target nucleic acids having different sequences. In some embodiments, a sequencing read is terminated when signals are no longer obtained from one or more target nucleic acid molecules from which signal acquisition was initiated. For example, a sequencing read can be initiated for one or more target nucleic acid molecules that are present on a solid phase substrate and terminated upon removal of the one or more target nucleic acid molecules from the substrate. Sequencing can be terminated by otherwise ceasing detection of the target nucleic acids that were present on the substrate when the sequencing run was initiated.

As used herein, the term "sequencing representation" and/or grammatical equivalents thereof can refer to information that signifies the order and type of monomeric units in the polymer. For example, the information can indicate the order and type of nucleotides in a nucleic acid. The information can be in any of a variety of formats including, for example, a depiction, image, electronic medium, series of symbols, series of numbers, series of letters, series of colors, etc. The information can be at single monomer resolution or at lower resolution, as set forth in further detail below. An exemplary polymer is a nucleic acid, such as DNA or RNA, having nucleotide units. A series of "A," "T," "G," and "C" letters is a well known sequence representation for DNA that can be correlated, at single nucleotide resolution, with the actual sequence of a DNA molecule. Other exemplary polymers are proteins having amino acid units and polysaccharides having saccharide units.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

Transposon Sequences

Some embodiments provided herein include transposon sequences. In some embodiments, a transposon sequence includes at least one transposase recognition site and at least one barcode. In some embodiments, a transposon sequence includes a first transposon recognition site, a second transposon recognition site, and a barcode disposed therebetween. FIG. 1A depicts a schematic a transposon sequence.

Figure 1B:
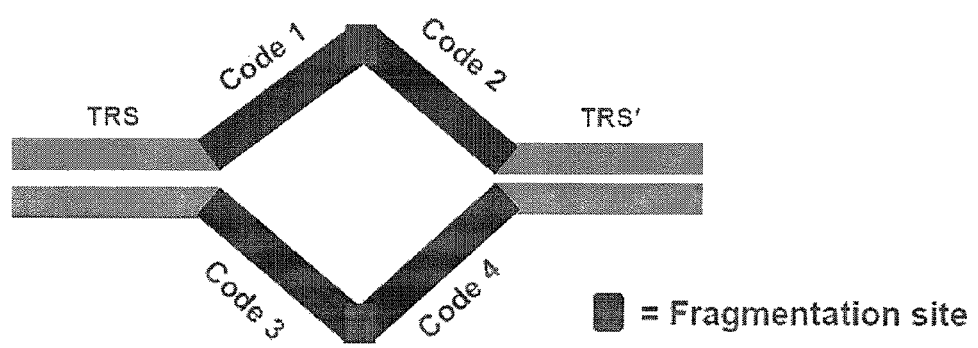
FIG. 1B depicts a double-stranded transposon sequence comprising transposon recognition sites (TRS and TRS'), a fragmentation site, and a barcode comprising four barcode sequences (CODE 1, CODE 2, CODE 3, and CODE 4). In the embodiment shown, CODE 1 and CODE 3, and CODE 2 and CODE 4 are non-complementary sequences.

A transposase recognition site can include two complementary nucleic acid sequences, e.g., a double-stranded nucleic acid or a hairpin nucleic acid, that comprise a substrate for a transposase or integrase. As will be understood, in some embodiments, a transposon sequence can include at least a portion comprising single-stranded nucleic acid sequences, and/or at least a portion comprising non-complementary sequences. An exemplary embodiment of a transposon sequence comprising a double-stranded nucleic acid comprising non-complementary strands is depicted in FIG. 1B.

The transposase or integrase may bind to the transposase recognition site and insert the transposase recognition site into a target nucleic acid. In some such insertion events, one strand of the transposase recognition site may be transferred into the target nucleic acid.

In some embodiments a transposase recognition site is a component of a transposition system. A transposition system can include a transposase enzyme and a transposase recognition site. In some such systems, the transposase can form a functional complex with a transposes recognition site that is capable of catalyzing a transposition reaction. Some embodiments can include the use of a hyperactive Tn5 transposase and a Tn5-type transposase recognition site (Goryshin, I. and Reznikoff, W. S., J. Biol. Chem., 273: 7367, 1998), or MuA transposase and a Mu transposase recognition site comprising R1 and R2 end sequences (Mizuuchi, K., Cell, 35: 785, 1983; Savilahti, H, et al., EMBO J., 14: 4893, 1995). An exemplary transposase recognition site that forms a complex with a hyperactive Tn5 transposase (e.g., EZ-Tn5™ Transposase, EPICENTRE Biotechnologies, Madison, Wis., USA) comprises the following transferred strand and non-transferred strands: 5' AGATGTGTATAAGAGACAG 3', (SEQ ID NO: 1), 5' CTGTCT CTTATACACATCT 3' (SEQ ID NO: 2), respectively. More examples of transposition systems that can be used with certain embodiments provided herein include *Staphylococcus aureus* Tn552 (Colegio O R et al., J. Bacteriol., 183: 2384-8, 2001; Kirby C et al., Mol. Microbiol., 43: 173-86, 2002), Ty1 (Devine S E, and Boeke J D., Nucleic Acids Res., 22: 3765-72, 1994 and International Patent Application No. WO 95/23875), Transposon Tn7 (Craig, N L, Science. 271: 1512, 1996; Craig, N L, Review in: Curr Top Microbiol Immunol., 204: 27-48, 1996), Tn/O and IS10 (Kleckner N, et al., Curr Top Microbiol Immunol., 204: 49-82, 1996), Mariner transposase (Lampe D J, et al., EMBO J., 15: 5470-9, 1996), Tc1 (Plasterk R H, Curr Top Microbiol Immunol, 204: 125-43, 1996), P Element (Gloor, G B, Methods Mol. Biol., 260: 97-114, 2004), Tn3 (Ichikawa H, and Ohtsubo E., J Biol. Chem. 265: 18829-32, 1990), bacterial insertion sequences (Ohtsubo, F and Sekine, Y, Curr. Top. Microbiol. Immunol. 204: 1-26, 1996), retroviruses (Brown P O, et al., Proc Natl Acad Sci USA, 86: 2525-9, 1989), and retrotransposon of yeast (Boeke J D and Corces V G, Annu Rev Microbiol. 43: 403-34, 1989, the disclosures of which are incorporated herein by reference in their entireties). More examples include IS5, Tn10, Tn903, IS911, and engineered versions of transposase family enzymes (Zhang et al., (2009) PLoS Genet. 5:e1000689. Epub 2009 Oct. 16; Wilson C. et al (2007) J. Microbiol Methods 71:332-5, the disclosures of which are incorporated herein by reference in their entireties).

Barcodes

Generally, a barcode can include one or more nucleotide sequences that can be used to identify one or more particular nucleic acids. A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70, 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated.

In some embodiments, a transposon sequence comprises at least one barcode. In some embodiments, a transposon sequence comprises a barcode comprising a first barcode sequence and a second barcode sequence. In some such embodiments, the first barcode sequence can be identified or designated to be paired with the second barcode sequence. For example, a known first barcode sequence can be known to be paired with a known second barcode sequence using a reference table comprising a plurality of first and second bar code sequences known to be paired to one another. In another example, the first barcode sequence can comprise the same sequence as the second barcode sequence. In another example, the first barcode sequence can comprise the reverse complement of the second barcode sequence. In some embodiments, the first barcode sequence and the second barcode sequence are different.

In some embodiments, a transposon sequence can comprise a plurality of different barcode sequences. For example, in a transposon sequence comprising a double-strand nucleic acid, each strand can comprise a different barcode sequence. As will be understood, such a transposon sequence can be useful to inhibit insertion of other sequences into the transposon sequence by transposition. Such transposon sequences can also be used to tag particular strands of a double-stranded target nucleic acid, for example in methods that include haplotypes sequencing. An exemplary transposon sequence comprising a plurality of barcode sequences is depicted in FIG. 1B.

In some embodiments, a population of nucleic acids can comprise nucleic acids that include a first barcode sequence and second barcode sequence. In some such embodiments the first and second barcode sequences of a particular nucleic acid can be different. As will be described further herein, paired first and second barcode sequences can be used to identify different nucleic acids comprising barcodes linked with one another.

Linkers

Some embodiments include transposon sequences comprising a first barcode sequence and a second barcode sequence having a linker disposed therebetween. In other embodiments, the linker can be absent, or can be the sugar-phosphate backbone that connects one nucleotide to another. The linker can comprise, for example, one or more of a nucleotide, a nucleic acid, a non-nucleotide chemical moiety, a nucleotide analogue, amino acid, peptide, polypeptide, or protein. In preferred embodiments, a linker comprises a nucleic acid. The linker can comprise at least about 1, 2, 3, 4, 5, 6, 7, 8, 9, 10, 11, 12, 13, 14, 15, 16, 17, 18, 19, 20, or more nucleotides. In some embodiments, a linker can comprise at least about 10, 20, 30, 40, 50, 60, 70, 80, 90, 100, or more nucleotides.

Fragmentation Sites

In some embodiments, the linker can comprise a fragmentation site. A fragmentation site can be used to cleave the physical, but not the informational association between a first barcode sequence and a second barcode sequence. Cleavage may be by biochemical, chemical or other means. In some embodiments, a fragmentation site can include a nucleotide or nucleotide sequence that may be fragmented by various means. For example, a fragmentation site may be a substrate for an enzyme, such as a nuclease, that will cleave the physical association between a first barcode sequence and a second barcode sequence. For example, the fragmentation site comprises a restriction endonuclease site and may be cleaved with an appropriate restriction endonuclease. In another example, a fragmentation site can comprise at least one ribonucleotide in a nucleic acid that may otherwise comprise deoxyribonucleotides and may be cleaved with an RNAse. Chemical cleavage agents capable of selectively cleaving the phosphodiester bond between a deoxyribonucleotide and a ribonucleotide include metal ions, for example rare-earth metal ions (e.g., $La^{3+}$, particularly $Tm^{3+}$, $Yb^{3+}$ or $Lu^{3+}$ (Chen et al. Biotechniques. 2002, 32: 518-520; Komiyama et al. Chem. Commun. 1999, 1443-1451)), Fe(3) or Cu(3), or exposure to elevated pH, e.g., treatment with a base such as sodium hydroxide. As used herein, selective cleavage of the phosphodiester bond between a deoxyribonucleotide and a ribonucleotide can refer to the chemical cleavage agent is not capable of cleaving the phosphodiester bond between two deoxyribonucleotides under the same conditions.

In another example, the fragmentation site can comprise one or more recognition sequences for a nickase, that is, a nicking endonuclease that breaks one strand of a double-stranded nucleic acid. Thus, the fragmentation site can comprise a first nickase recognition sequence, a second nickase recognition sequence. The cut site for each recognition sequence can be the same site or different site.

In another example, a fragmentation site can include one or more nucleotide analogues that comprise an abasic site and permits cleavage at the fragmentation site in the presence of certain chemical agents, such as polyamine, N,N'-dimethylethylenediamine (DMED) (U.S. Patent Application Publication No. 2010/0022403, incorporated by reference herein). In some embodiments, an abasic site may be created within a fragmentation site by first providing a fragmentation site comprising a deoxyuridine (U) of a double stranded nucleic acid. The enzyme uracil DNA glycosylase (UDG) may then be used to remove the uracil base, generating an abasic site on one strand. The polynucleotide strand including the abasic site may then be cleaved at the abasic site by treatment with endonuclease (e.g. Endo IV endonuclease, AP lyase, FPG glycosylase/AP lyase, Endo VIII glycosylase/AP lyase), heat or alkali. Abasic sites may also be generated at nucleotide analogues other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. Endo IV, AP lyase). (U.S. Patent Application Publication No. 2011/0014657, incorporated by reference herein in its entirety).

In another example, a fragmentation site may include a diol linkage which permits cleavage by treatment with periodate (e.g., sodium periodate). In another example, a fragmentation site may include a disulphide group which permits cleavage with a chemical reducing agent, e.g. Tris(2-carboxyethyl)-phosphate hydrochloride (TCEP).

In some embodiments, a fragmentation site may include a cleavable moiety that may be subject to photochemical cleavage. Photochemical cleavage encompasses any method which utilizes light energy in order to achieve cleavage of nucleic acids, for example, one or both strands of a double-stranded nucleic acid molecule. A site for photochemical cleavage can be provided by a non-nucleotide chemical moiety in a nucleic acid, such as phosphoramidite[4-(4,4'-dimethoxytrityloxy)butyramidomethyl)-1-(2-nitrophenyl)-ethyl]-2-cyanoethyl-(N,N-diisopropyl)-phosphoramidite) (Glen Research, Sterling, Va., USA, Cat No. 10-4913-XX).

In some embodiments, a fragmentation site can include a peptide, for example, conjugate structure in which a peptide molecule is linked to a nucleic acid. The peptide molecule can subsequently be cleaved by a peptidase enzyme of the appropriate specificity, or any other suitable means of non-enzymatic chemical or photochemical cleavage. In some embodiments, a conjugate between peptide and nucleic acid will be formed by covalently linking a peptide to a nucleic acid, e.g., a strand of a double-stranded nucleic acid. Conjugates between a peptide and nucleic acid can be prepared using techniques generally known in the art. In one such technique the peptide and nucleic acid components of the desired amino acid and nucleotide sequence can be synthesized separately, e.g. by standard automated chemical synthesis techniques, and then conjugated in aqueous/organic solution. By way of example, the OPeC™ system commercially available from Glen Research is based on the native ligation of an N-terminal thioester-functionalized peptide to a 5'-cysteinyl oligonucleotide.

Primer Sites

In some embodiments, a linker can be a "sequencing adaptor" or "sequencing adaptor site", that is to say a region that comprises one or more sites that can hybridize to a primer. In some embodiments, a linker comprises at least a first primer site. In some embodiments, a linker comprises at least a first primer site and a second primer site. The orientation of the primer sites in such embodiments can be such that a primer hybridizing to the first primer site and a primer hybridizing to the second primer site are in the same orientation, or in different orientations. In one embodiment, the primer sequence in the linker can be complementary to a primer used for amplification. In another embodiment, the primer sequence is complementary to a primer used for sequencing.

In some embodiments, a linker can include a first primer site, a second primer site having a non-amplifiable site disposed therebetween. The non-amplifiable site is useful to block extension of a polynucleotide strand between the first and second primer sites, wherein the polynucleotide strand hybridizes to one of the primer sites. The non-amplifiable site can also be useful to prevent concatamers. Examples of non-amplifiable sites include a nucleotide analogue, non-nucleotide chemical moiety, amino-acid, peptide, and polypeptide. In some embodiments, a non-amplifiable site comprises a nucleotide analogue that does not significantly basepair with A, C, G or T.

Some embodiments include a linker comprising a first primer site, a second primer site having a fragmentation site disposed therebetween.

Figure 12:
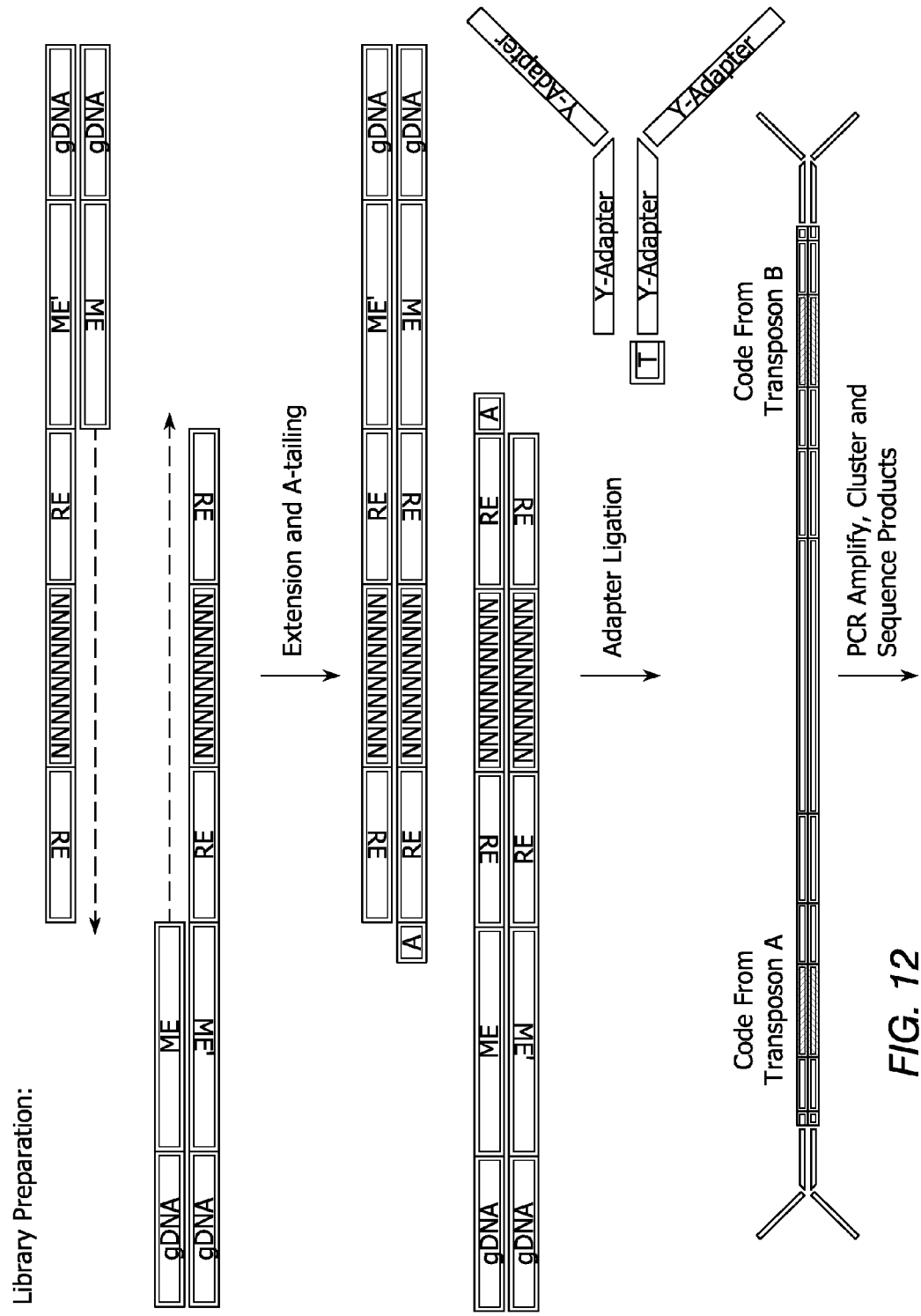
FIG. 12 depicts a library preparation method that involves ligation of a forked adapter sequence. Steps include: library preparation; extension and A-tailing; adapter ligation; and PCR amplify, cluster, and sequence products.

Other embodiments can use a forked or Y-shaped adapter design useful for directional sequencing, as described in U.S. Pat. No. 7,741,463, which is incorporated herein by reference, An example is shown in FIG. 12.

Affinity Tags

In some embodiments, a linker can comprise an affinity tag. Affinity tags can be useful for the bulk separation of target nucleic acids hybridized to hybridization tags. As used herein, the term "affinity tag" and grammatical equivalents can refer to a component of a multi-component complex, wherein the components of the multi-component complex specifically interact with or bind to each other. For example an affinity tag can include biotin or His that can bind streptavidin or nickel, respectively. Other examples of multiple-component affinity tag complexes include, ligands and their receptors, for example, avidin-biotin, streptavidin-biotin, and derivatives of biotin, streptavidin, or avidin, including, but not limited to, 2-iminobiotin, desthiobiotin, NeutrAvidin (Molecular Probes, Eugene, Oreg.), CaptAvidin (Molecular Probes), and the like; binding proteins/peptides, including maltose-maltose binding protein (MBP), calcium-calcium binding protein/peptide (CBP); antigen-antibody, including epitope tags, including c-MYC (e.g., EQKLISEEDL (SEQ ID NO: 3)), HA (e.g., YPYDVPDYA (SEQ ID NO: 4)), VSV-G (e.g., YTDIEMNRLGK (SEQ ID NO: 5)), HSV (e.g., QPELAPEDPED (SEQ ID NO: 6)), V5 (e.g., GKPIPN-PLLGLDST (SEQ ID NO: 7)), and FLAG Tag™. (e.g., DYKDDDDKG (SEQ ID NO: 8)), and their corresponding anti-epitope antibodies; haptens, for example, dinitrophenyl and digoxigenin, and their corresponding antibodies; aptamers and their corresponding targets; poly-His tags (e.g., penta-His and hexa-His) and their binding partners including corresponding immobilized metal ion affinity chromatography (IMAC) materials and anti-poly-His antibodies; fluorophores and anti-fluorophore antibodies; and the like.

Reporter Moieties

In some embodiments, a linker can comprise a reporter moiety. As used herein, the term "reporter moiety" and grammatical equivalents can refer to any identifiable tag, label, or group. The skilled artisan will appreciate that many different species of reporter moieties can be used with the methods and compositions described herein, either individually or in combination with one or more different reporter moieties. In certain embodiments, a reporter moiety can emit a signal. Examples of signals fluorescent, a chemiluminescent, a bioluminescent, a phosphorescent, a radioactive, a calorimetric, or an electrochemiluminescent signals. Example reporter moieties include fluorophores, radioisotopes, chromogens, enzymes, antigens including epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer compatible reporter moieties, such as mass tags, charge tags, and isotopes. More reporter moieties that may be used with the methods and compositions described herein include spectral labels such as fluorescent dyes (e.g., fluorescein isothiocyanate, Texas red, rhodamine, and the like), radiolabels (e.g., $^3$H, $^{125}$I $^{35}$S, $^{14}$C, $^{32}$P, $^{33}$P, etc.), enzymes (e.g., horse-radish peroxidase, alkaline phosphatase etc.) spectral calorimetric labels such as colloidal gold or colored glass or plastic (e.g. polystyrene, polypropylene, latex, etc.) beads; magnetic, electrical, thermal labels; and mass tags. Reporter moieties can also include enzymes (horseradish peroxidase, etc.) and magnetic particles. More reporter moieties include chromophores, phosphors and fluorescent moieties, for example, Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking to an element desirably detected in an apparatus or assay provided herein, or which can be modified to incorporate such functionalities include, e.g., dansyl chloride; fluoresceins such as 3,6-dihydroxy-9-phenylxanthydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine: N,N'-dihexyl oxacarbocyanine; merocyanine, 4-(3'-pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis(2-methyl-5-phenyl-oxazolyl)) benzene; 6-dimethylamino-1,2-benzophenazin; retinol; bis (3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-(p-(2benzimidazolyl)-phenyl)maleimide; N-(4-fluoranthyl)maleimide; bis(homovanillic acid); resazarin; 4-chloro7-nitro-2,1,3-benzooxadiazole; merocyanine 540; resorufin; rose bengal; 2,4-diphenyl-3(2H)-furanone, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Pat. No. 6,544,732, hereby incorporated by reference), pyrene, Malachite green, stilbene, Lucifer Yellow, Cascade Blue™, Texas Red, Cy dyes (Cy3, Cy5, etc.), Alexa Fluor® dyes, phycoerythin, bodipy, and others described in the 6th Edition of the Molecular Probes Handbook by Richard P. Haugland, expressly incorporated by reference herein.

Certain Methods of Making Transposon Sequences

The transposon sequences provided herein can be prepared by a variety of methods. Example methods include direct synthesis and hairpin extension methods. In some embodiments, transposon sequences may be prepared by direct synthesis. For example, a transposon sequence comprising a nucleic acid may be prepared by methods comprising chemical synthesis. Such methods are well known in the art, e.g., solid phase synthesis using phophoramidite precursors such as those derived from protected 2'-deoxynucleosides, ribonucleosides, or nucleoside analogues.

In some embodiments, a transposon sequence can be prepared by hairpin extension. In some such embodiments, a portion of a transposon sequence may be prepared by chemical synthesis and extended by hairpin extension. In an example embodiment, a precursor transposon sequence comprising a polynucleotide may include a first transposase recognition site, and a first barcode sequence. The precursor transposon sequence may be extended using an appropriate nucleic acid polymerase by hairpin extension, thereby preparing a hairpin structure comprising a first transposase recognition site, a first barcode sequence, a second barcode sequence, and a second transposase recognition site. In such a transposon sequence, the first transposase recognition site and first barcode sequence can have the reverse complement sequence of, and the second transposase recognition site and the second barcode sequence, respectively.

Some methods of preparing transposons sequences can include preparing barcode sequences. Barcode sequences can be generated randomly and non-randomly. Some barcode sequences may or may not include sequences likely to be found in a target nucleic acid. Some barcode sequences may or may not include restriction sites. In some embodiments, at least a portion of a barcode sequence can be generated randomly. In some embodiments a barcode sequence can be generated using combinatorial methods. In some such methods, barcode sequences can comprise one or more subunits comprising one or more consecutive nucleotides. As will be understood, in some embodiments, a subunit can comprise a nucleotide analogue and/or a nucleotide comprising a label. At least a portion of a barcode sequence can comprise at least one subunit. Barcode sequences comprising at least one subunit can be generated randomly or non-randomly. In some embodiments, at least a portion of a barcode sequences comprising at least one subunit can be generated randomly or non-randomly. As will be understood, in some embodiments, at least a portion of a barcode sequence is known.

Figure 2:
FIG. 2 depicts an exemplary scheme to prepare a transposon sequence.
Figure 2:
Figure 2:
Figure 2:
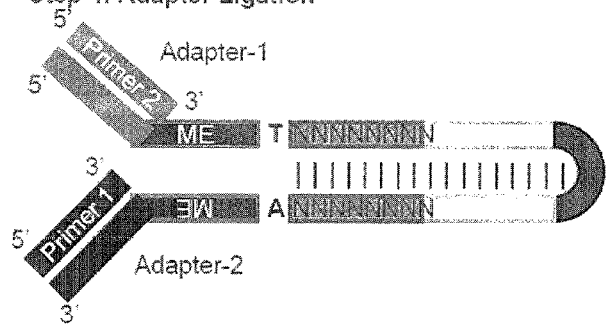
Figure 2:
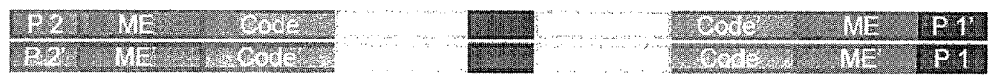

Primer sites may be ligated to the ends of the hairpin structure in order to generate a complementary strand to the single-strand of the hairpin structure. An exemplary embodiment of a method of making a transposon sequence is depicted in FIG. 2. It will be understood that the primer sites introduced to generate the complementary strand may be removed by a transposase during a transposition reaction.

Figure 14:
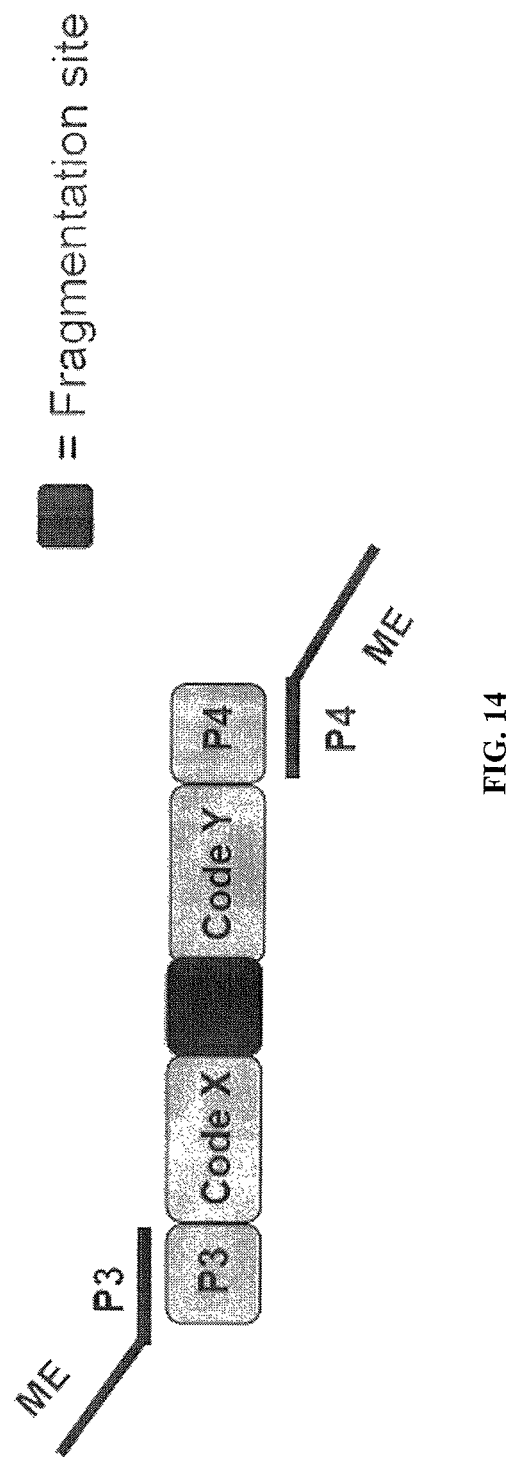
FIG. 14 depicts a method of preparing a transposon sequence which includes the use of tailed-oligonucleotides comprising mosaic elements (ME). The transposon sequence includes primer sites P3 and P4, a barcode comprising Code X and Code Y, and a fragmentation site.

In some embodiments, methods of making transposon sequences can include incorporating sequences using amplification methods. Templates for amplification that include barcode sequences can be prepared by a variety of systems, for example, using in situ oligonucleotide arrays. Some methods of making transposon sequences include the use of tailed-oligonucleotides to incorporate sequences into a transposon sequence. An exemplary embodiment is depicted in FIG. 14. In FIG. 14 tailed-oligonucleotides comprising mosaic elements (ME) may be used to prepare a transposon sequence comprising a barcode comprising Code X and Code Y, and a linker comprising a fragmentation site.

Target Nucleic Acids

A target nucleic acid can include any nucleic acid of interest. Target nucleic acids can include DNA, RNA, peptide nucleic acid, morpholino nucleic acid, locked nucleic acid, glycol nucleic acid, threose nucleic acid, mixtures thereof, and hybrids thereof. In a preferred embodiment, genomic DNA fragments or amplified copies thereof are used as the target nucleic acid. In another preferred embodiment, mitochondrial or chloroplast DNA is used.

A target nucleic acid can comprise any nucleotide sequence. In some embodiments, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500, 1000 nucleotides or more. Repeat sequences can be repeated, either contiguously or non-contiguously, any of a variety of times including, for example, 2, 3, 4, 5, 6, 7, 8, 9, 10, 15, 20 times or more.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats so that reagents are delivered simultaneously to the target nucleic acids, for example, in one or more chambers or on an array surface. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces genera*); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (for example, *Caenorhabditis elegans*), and mammals (for example, rat, mouse, monkey, non-human primate and human)).

Methods of Preparing Template Nucleic Acids

Some embodiments include methods of preparing template nucleic acids. As used herein, the term "template nucleic acid" can refer to a target nucleic acid, a fragment thereof, or any copy thereof comprising at least one transposon sequence, a fragment thereof, or any copy thereof. Accordingly, some methods of preparing template nucleic acids include inserting a transposon sequence into a target nucleic acid, thereby preparing a template nucleic acid. Some methods of insertion include contacting a transposon sequence provided herein with a target nucleic acid in the presence of an enzyme, such as a transposase or integrase, under conditions sufficient for the integration of the transposon sequence into the target nucleic acid.

Exemplary transposition systems that may be utilized with the compositions and methods provided herein include a hyperactive Tn5 transposase and a Tn5-type transposase recognition site (Goryshin, I. and Reznikoff, W. S., J. Biol. Chem., 273: 7367, 1998; US Pub. 2010/0120098, which is incorporated herein by reference), and MuA transposase and a Mu transposase recognition site comprising R1 and R2 end sequences (Mizuuchi, K., Cell, 35: 785, 1983; Savilahti, H, et al., EMBO J., 14: 4893, 1995). More examples include sequences and enzymes related to *Staphylococcus aureus* Tn552 (Colegio O R et al., J. Bacteriol., 183: 2384-8, 2001; Kirby C et al., Mol. Microbiol., 43: 173-86, 2002), Ty1 (Devine S E, and Boeke J D., Nucleic Acids Res., 22: 3765-72, 1994 and International Patent Application No. WO 95/23875), Transposon Tn7 (Craig, N L, Science. 271: 1512, 1996; Craig, N L, Review in: Curr Top Microbiol Immunol., 204: 27-48, 1996), Tn/O and IS10 (Kleckner N, et al., Curr Top Microbiol Immunol., 204: 49-82, 1996), Mariner transposase (Lampe D J, et al., EMBO J., 15: 5470-9, 1996), Tc1 (Plasterk R H, Curr Top Microbiol Immunol, 204: 125-43, 1996), P Element (Gloor, G B, Methods Mol. Biol., 260: 97-114, 2004), Tn3 (Ichikawa H, and Ohtsubo E., J Biol. Chem. 265: 18829-32, 1990), bacterial insertion sequences (Ohtsubo, F and Sekine, Y, Curr. Top. Microbiol. Immunol. 204: 1-26, 1996), retroviruses (Brown P O, et al., Proc Natl Acad Sci USA, 86: 2525-9, 1989), and retrotransposon of yeast (Boeke J D and Corces V G, Annu Rev Microbiol. 43: 403-34, 1989). More examples include IS5, Tn10, Tn903, IS911, and engineered versions of transposase family enzymes (Zhang et al., (2009) PLoS Genet. 5:e1000689. Epub 2009 Oct. 16; Wilson C. et al (2007) J. Microbiol Methods 71:332-5, the disclosures of which are incorporated herein by reference in their entireties).

In some embodiments, insertion of transposon sequences into a target nucleic acid can be non-random. In some embodiments, transposon sequences can be contacted with target nucleic acids comprising proteins that inhibit integration at certain sites. For example, transposon sequences can be inhibited from integrating into genomic DNA comprising proteins, genomic DNA comprising chromatin, genomic DNA comprising nucleosomes, or genomic DNA comprising histones. In some embodiments, transposon sequences can be associated with affinity tags in order to integrate the transposon sequence at a particular sequence in a target nucleic acid. For example, a transposon sequence may be associated with a protein that targets specific nucleic acid sequences, e.g., histones, chromatin-binding proteins, transcription factors, initiation factors, etc., and antibodies or antibody fragments that bind to particular sequence-specific nucleic-acid-binding proteins. In an exemplary embodiment, a transposon sequence is associated with an affinity tag, such as biotin; the affinity tag can be associated with a nucleic-acid-binding protein.

Figure 3:
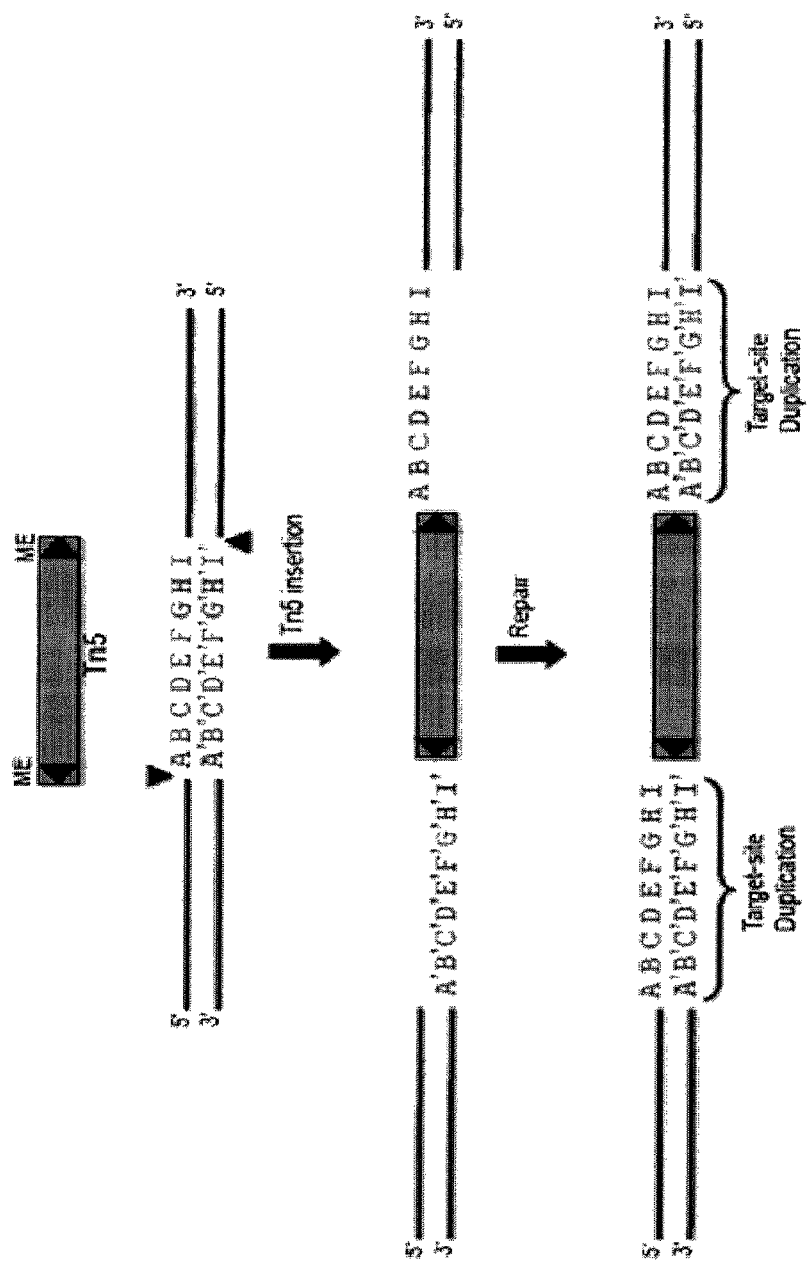
FIG. 3 depicts the integration of an exemplary Tn5 transposon comprising transposase recognition sequences (indicated by mosaic elements ME) into a target nucleic acid. The insertion results in duplication of the integration site, shown as single-stranded A'B'C'D'E'F'G'H'I' and single-stranded ABCDEFGHI. The figure also shows an optional repair step to fill in the single-stranded region. In some embodiments, the filled-in region can be used as a host tag.

It will be understood that during integration of some transposon sequences into a target nucleic acid, several consecutive nucleotides of the target nucleic acid at the integration site are duplicated in the integrated product. Thus the integrated product can include a duplicated sequence at each end of the integrated sequence in the target nucleic acid. An example of such a duplication event is depicted in FIG. 3. As used herein, the term "host tag" can refer to a target nucleic acid sequence that is duplicated at each end of an integrated transposon sequence. Single-stranded portions of nucleic acids that may be generated by the insertion of transposon sequences can be repaired by a variety of methods well known in the art, for example by using ligases, oligonucleotides and/or polymerases.

In some embodiments, a plurality of the transposon sequences provided herein is inserted into a target nucleic acid. Some embodiments include selecting conditions sufficient to achieve integration of a plurality of transposon sequences into a target nucleic acid such that the average distance between each integrated transposon sequence comprises a certain number of consecutive nucleotides in the target nucleic acid.

In some embodiments, conditions for insertion of transposon sequences are sufficient to reduce the likelihood of forming concatameric complexes comprising a transposase associated with more than one transposon sequence. In one example, complexes comprising a transposase and a transposon sequence can be formed under dilute conditions; subsequent steps of inserting the transposon sequences into a target nucleic acid may be carried out at higher concentrations of transposase/transposon sequence complex. In another example, transposase/transposon sequence complexes can be prepared by contacting a circular transposon sequence with a transposase. As will be understood, the transposon sequence may be linearized during formation of the transposase/transposon sequence complex. In another example, a transposase/transposon sequence complex may be prepared by preparing complexes comprising partial transposon sequences comprising a transposon recognition site, and contacting the partial sequences with transposase monomers. Two partial transposon sequences may be ligated to one another to prepare a whole transposon sequence associated with a transposase comprising a dimer.

Some embodiments include selecting conditions sufficient to achieve insertion of a transposon sequence into a target nucleic acid, but not into another transposon sequence. A variety of methods can be used to reduce the likelihood that a transposon sequence inserts into another transposon sequence. For example, transposon sequences can comprise thiophosphate-modified nucleic acids. In another example, a transposon sequence can comprise a DNA/RNA hybrid, such as an RNA transposon sequence comprising DNA transposase recognition sites. In another example, a transposon sequence comprises a single-stranded sequence, further comprising double-stranded transposase recognition sites. It will be appreciated that more methods can include transposon sequences comprising single-stranded nucleic acids to inhibit insertion into the transposon sequence; transposon sequences comprising RNA to inhibit insertion into the transposon sequence; and transposon sequences associated with nucleic acid binding proteins to inhibit insertion into the transposon sequence.

In some embodiments, conditions may be selected so that the average distance in a target nucleic acid between integrated transposon sequences is at least about 5, 10, 20, 30, 40, 50, 60, 70, 80, 90, 100, or more consecutive nucleotides. In some embodiments, the average distance in a target nucleic acid between integrated transposon sequences is at least about 100, 200, 300, 400, 500, 600, 700, 800, 900, 1000, or more consecutive nucleotides. In some embodiments, the average distance in a target nucleic acid between integrated transposon sequences is at least about 1 kb, 2 kb, 3 kb, 4 kb, 5 kb, 6 kb, 7 kb, 8 kb, 90 kb, 100 kb, or more consecutive nucleotides. In some embodiments, the average distance in a target nucleic acid between integrated transposon sequences is at least about 100 kb, 200 kb, 300 kb, 400 kb, 500 kb, 600 kb, 700 kb, 800 kb, 900 kb, 1000 kb, or more consecutive nucleotides. As will be understood, some conditions that may be selected include contacting a target nucleic acid with a certain number of transposon sequences.

Some embodiments include selecting conditions sufficient to achieve at least a portion of transposon sequences integrated into a target nucleic acid are different. In preferred embodiments, each transposon sequence integrated into a target nucleic acid is different. Some conditions that may be selected to achieve a certain portion of transposon sequences integrated into a target sequences that are different include selecting the degree of diversity of the population of transposon sequences. As will be understood, the diversity of transposon sequences arises in part due to the diversity of the barcodes of such transposon sequences. Accordingly, some embodiments include providing a population of transposon sequences in which at least a portion of the barcodes are different. In some embodiments, at least about 10%, 20%, 30%, 40%, 50%, 60%, 70%, 80%, 90%, 95%, 98%, 99%, or 100% of barcodes in a population of transposon sequences are different.

Some embodiments of preparing a template nucleic acid can include copying the sequences comprising the target nucleic acid. For example, some embodiments include hybridizing a primer to a primer site of a transposon sequence integrated into the target nucleic acid. In some such embodiments, the primer can be hybridized to the primer site and extended. The copied sequences can include at least one barcode sequence and at least a portion of the target nucleic acid. In some embodiments, the copied sequences can include a first barcode sequence, a second barcode sequence, and at least a portion of a target nucleic acid disposed therebetween. In some embodiments, at least one copied nucleic acid can include at least a first barcode sequence of a first copied nucleic acid that can be identified or designated to be paired with a second barcode sequence of a second copied nucleic acid. In some embodiments, the primer can include a sequencing primer. In some embodiments sequencing data is obtained using the sequencing primer.

Some embodiments of preparing a template nucleic acid can include amplifying sequences comprising at least a portion of one or more transposon sequences and at least a portion of a target nucleic acid. In some embodiments, at least a portion of a target nucleic acid can be amplified using primers that hybridize to primer sites of integrated transposon sequences integrated into a target nucleic acid. In some such embodiments, an amplified nucleic acid can include a first barcode sequence, and second barcode sequence having at least a portion of the target nucleic acid disposed therebetween. In some embodiments, at least one amplified nucleic acid can include at least a first barcode sequence of a first amplified nucleic acid that can be identified to be paired with a second barcode sequence of a second amplified sequence.

Some embodiments of preparing a template nucleic acid can include fragmenting a target nucleic acid comprising transposon sequences. Methods of fragmenting nucleic acids are well known in the art. In some embodiments, a nucleic acid comprising transposon sequences can be fragmented at random positions along the length of the nucleic acid. In some embodiments, a target nucleic acid comprising transposon sequences can be fragmented at the fragmentation sites of the transposon sequences. In some embodiments, insertion of a transposon sequence can include the duplication of the insertion site so that the inserted transposon sequence is disposed between duplicated single-stranded sequences (see, e.g., FIG. 3). In some embodiments, a polymerase may be used to cleave the fragmentation site. Examples of such polymerases include strand-displacing nucleic acid polymerases.

Further embodiments of preparing a template nucleic acid that include fragmenting a target nucleic acid comprising transposon sequences can also include amplifying the fragmented nucleic acids. In some embodiments, the fragmented nucleic acids can be amplified using primers that hybridize to primer sites of transposon sequences. In more embodiments, primer sites can be ligated to the ends of the fragmented nucleic acids. In some such embodiments, the fragmented nucleic acids with ligated primer sites can be amplified from such primer sites.

Some embodiments include reducing the complexity of a library of template nucleic acids. A complexity-reduction step can be performed before or after the fragmentation step in the method. For example, the target nucleic acid comprising the transposon sequences can be diluted so that a small number or a single molecule represents the target diluted before performing subsequent steps.

Figure 4:
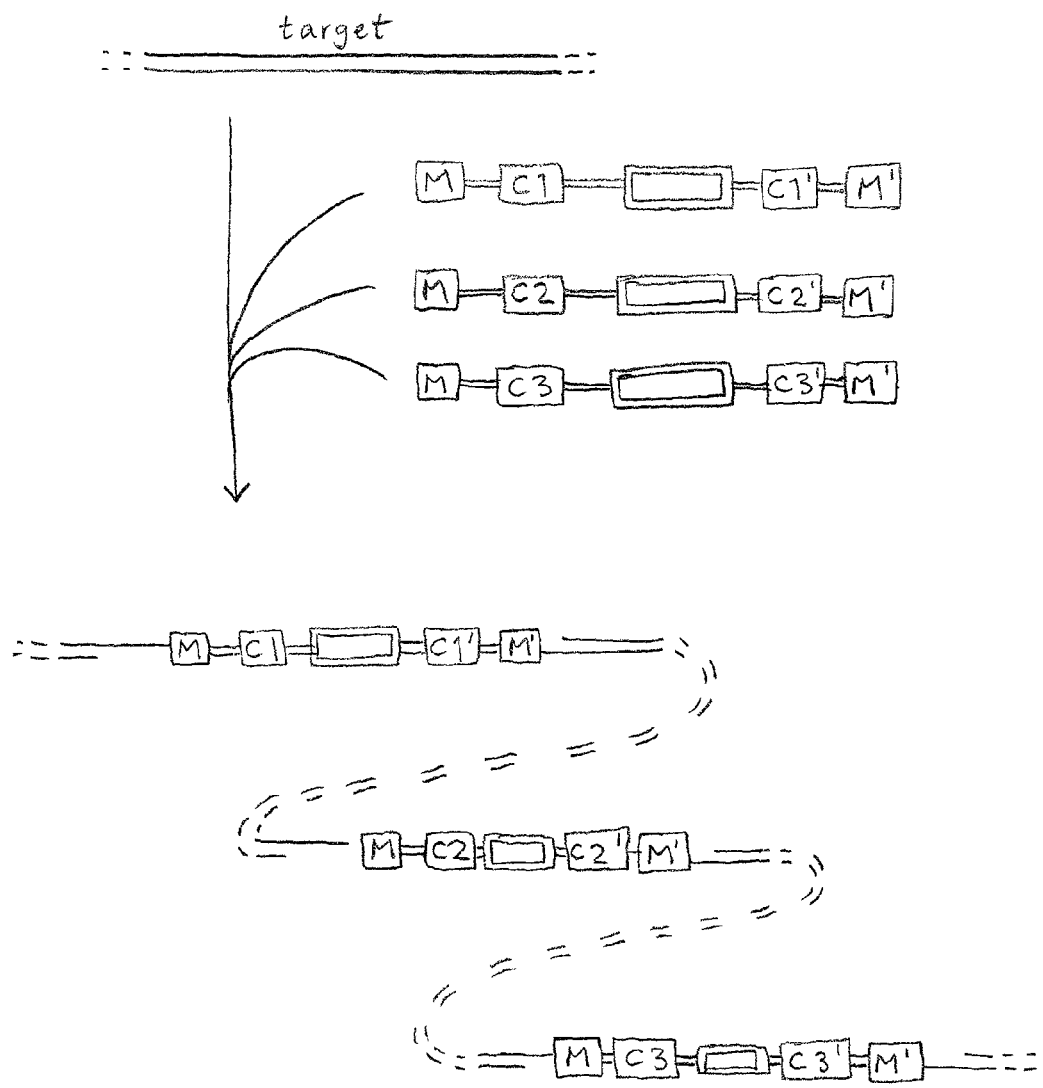
FIG. 4 depicts an exemplary embodiment of a contacting a target nucleic acid with a library of transposons, which integrates into the target nucleic acid.
Figure 5:
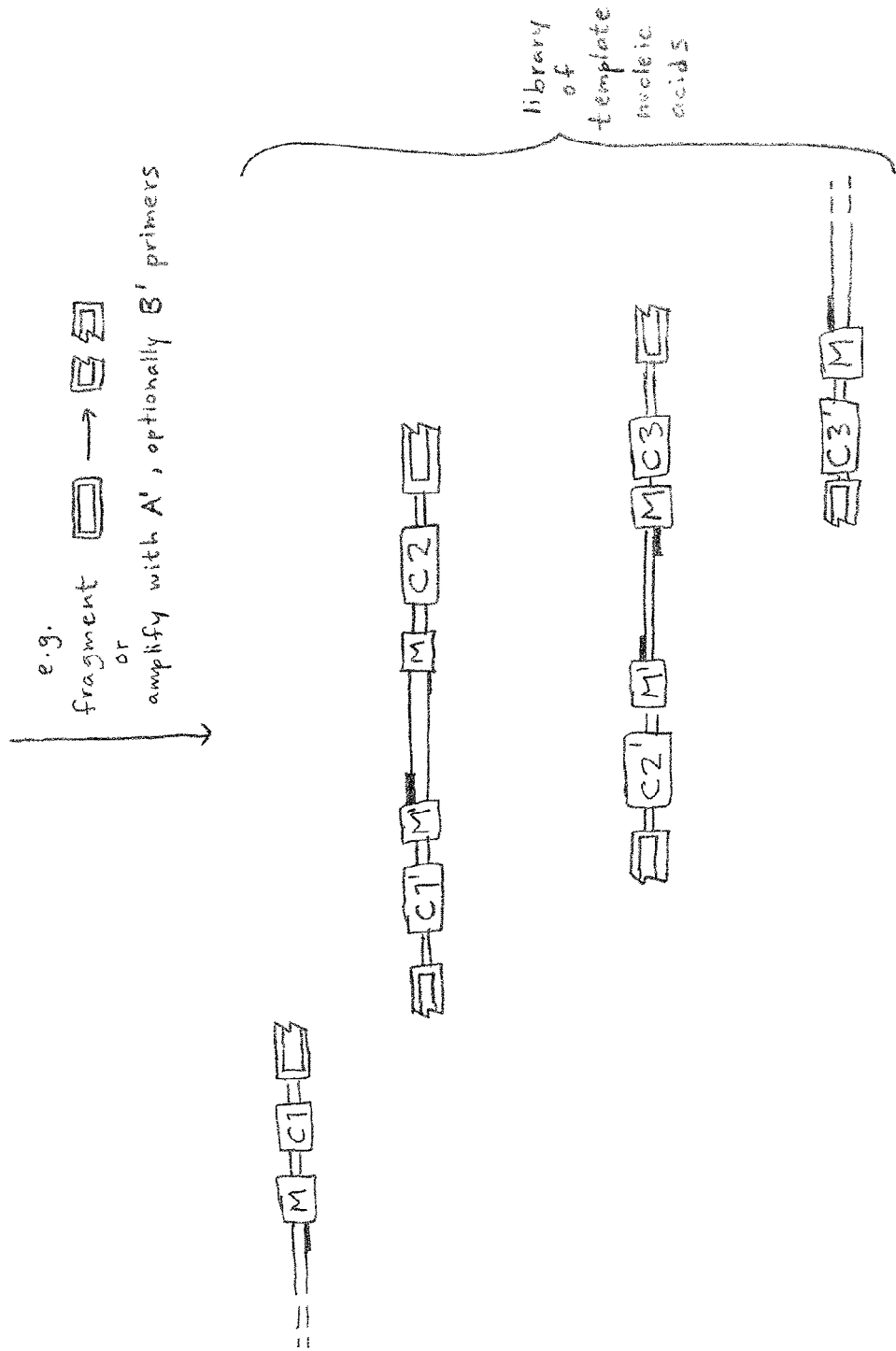
FIG. 5 depicts an optional step of fragmenting a linker into two parts, or an optional step of virtually fragmenting the linker by amplification using a primer A' and/or a primer B'. Fragmentation of the linker generates a library of template nucleic acids. In this figure, the filled-in region is indicated by a thick line.

FIG. 4 depicts an exemplary embodiment of a contacting a target nucleic acid with a library of transposons, which integrates into the target nucleic acid. FIG. 5 depicts an optional step of fragmenting a linker into two parts, or an optional step of virtually fragmenting the linker by amplification using a primer A' and/or a primer B'. Fragmentation of the linker generates a library of template nucleic acids. In this figure, the filled-in region is indicated by a thick line.

Figure 13:
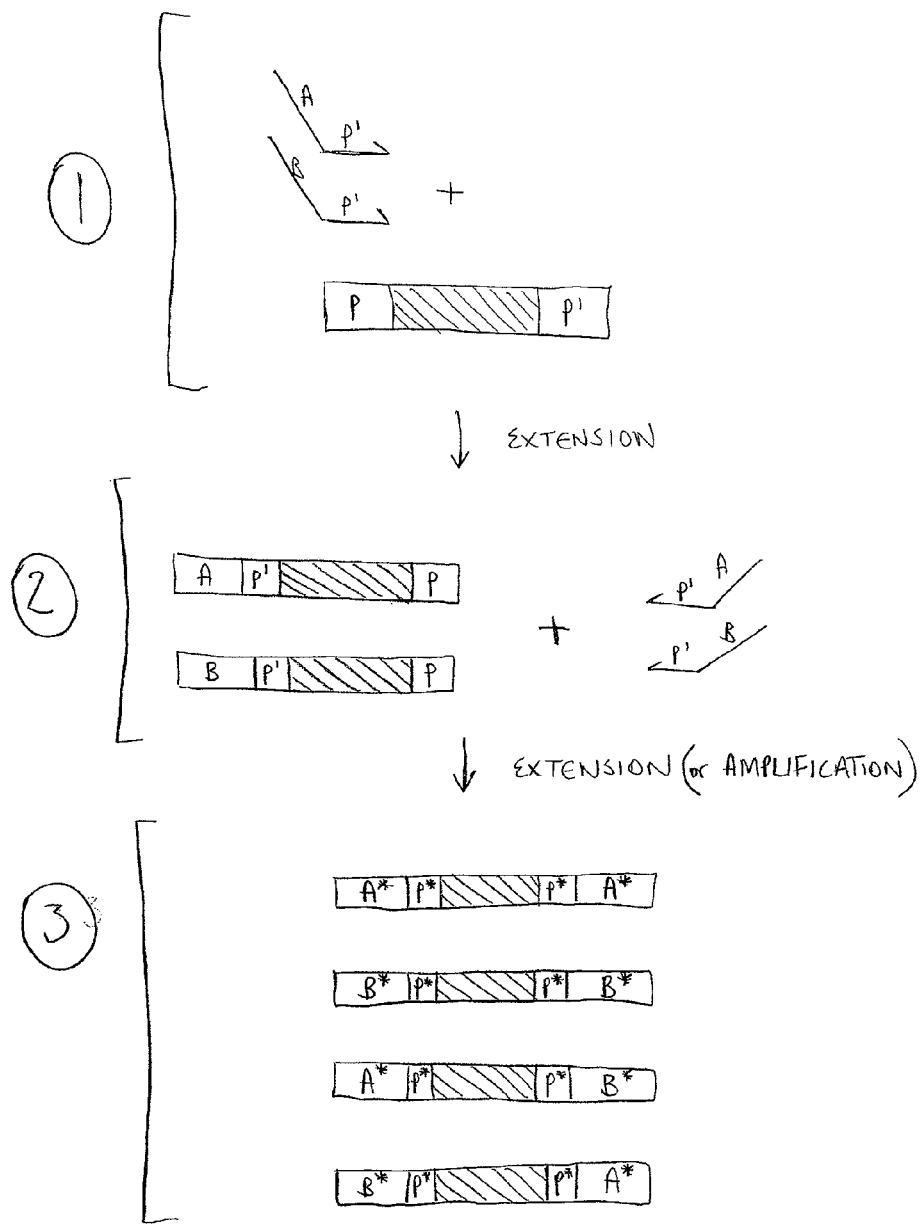
FIG. 13 depicts an exemplary embodiment using tailed-oligonucleotides to obtain a population of template nucleic acids comprising a first universal primer site (A) and a second universal primer site (B). In step 1, tailed-oligonucleotides comprising universal primer site sequences anneal to a template nucleic acid comprising primer site sequences (P and P') and are extended. In step 2, the tailed oligonucleotides of step 1 may anneal to the products of step 1 and be extended. Alternatively, step 2 can include an amplification step with the inclusion of oligonucleotides (e.g., oligonucleotides comprising A' and B' sequences). The products of step 2 are depicted in step 3.

In some embodiments, it can be advantageous for each template nucleic acid to incorporate at least one universal primer site. For example, a template nucleic acid can include first end sequences that comprise a first universal primer site, and second end sequences that comprise a second universal primer site. Universal primer sites can have various applications, such as amplifying, sequencing, and/or identifying one or more template nucleic acids. The first and second universal primer sites can be the same, substantially similar, similar, or different. In some embodiments, in order to prepare a template nucleic acid comprising a first universal primer site and a second universal primer site, a transposon sequence is prepared that includes a first transposase recognition site, a second transposase recognition site, a barcode disposed therebetween, wherein the barcode comprises a first barcode sequence and a second barcode sequence, separated by a linker. The linker includes a first primer site and a second primer site with a fragmentation site therebetween. The first primer site can comprise sequences that are the reverse complement of sequences within the second primer. In some embodiments, the first primer site comprises sequences having dyad symmetry to sequences within the second primer. In some embodiments, the first primer site comprises sequences having $C_2$ symmetry to sequences within the second primer. A plurality of transposons may be inserted into a target nucleic acid by transposition in the presence of a transposase. The incorporated sequences may be cleaved to yield a plurality of target nucleic acids, each comprising the first primer site and second primer site. In some embodiments, a first universal primer site and a second universal primer site can be incorporated into each template nucleic acid by a variety of methods. For example, template nucleic acids can be amplified using the first primer site and second primer site using tailed-oligonucleotides. As is understood in the art, a tailed-oligonucleotide can include sequences complementary to a primer site and additional sequences. In an example embodiment, a first tailed-oligonucleotide comprises sequences complementary to a first primer site and sequences for a first universal primer site, and a second tailed-oligonucleotide comprises sequences complementary to a second primer site and sequences for a second universal primer site. FIG. 13 depicts an example embodiment series of rounds of extending template using tailed-oligonucleotides to obtain a population of template nucleic acids comprising template nucleic acids that include a first universal primer site and a second universal primer site. With respect to FIG. 13, in step 1, oligonucleotides comprising either a first universal primer sequence (A) or a second universal primer sequence (B) anneal to a primer site (P) of a template nucleic acid, and are extended. In step 2, the extension products provide templates for a further extension step. Alternatively, the extension products can be amplified with the use of additional oligonucleotides. The products of step 2 are depicted in step 3 and include nucleic acid sequences comprising first universal primer sites only, second universal primer sites only, or first and second universal primer sites. As will be understood, nucleic acid sequences comprising a first universal primer site and second universal primer site may be used in further sequencing methods.

It will be understood that in some embodiments, the vast number of available barcodes permits each template nucleic acid molecule to comprise a unique identification. Unique identification of each molecule in a mixture of template nucleic acids can be used in several applications to identify individual nucleic acid molecules, in samples having multiple chromosomes, genomes, cells, cell types, cell disease states, and species, for example in haplotype sequencing, parental allele discrimination, metagenomic sequencing, and sample sequencing of a genome.

Methods of Analyzing Template Nucleic Acids

Some embodiments include methods of analyzing template nucleic acids. Sequencing information can be obtained from a template nucleic acids and a sequence representation of the target nucleic acid can be obtained from such sequencing data.

In some embodiments, a linked read strategy may be used. A linked read strategy can include identifying sequencing data that links at least two sequencing reads. For example, a first sequencing read may contain a first marker, and a second sequencing read may contain a second marker. The first and second markers can identify the sequencing data from each sequencing read to be adjacent in a sequence representation of the target nucleic acid. In some embodiments, markers can comprise a first barcode sequence and a second barcode sequence in which the first barcode sequence can be paired with the second barcode sequence. In more embodiments, markers can comprise a first host tag and a second host tag. In more embodiments, markers can comprise a first barcode sequence with a first host tag, and a second barcode sequence with a second host tag.

An exemplary embodiment of a method for sequencing a template nucleic acid can comprise the following steps. First, sequence the first barcode sequence using a primer hybridizing to the first primer site as the sequencing primer; second, sequence the second barcode sequence using a primer hybridizing to the second primer site as the sequencing primer. The result is two sequence reads that help link the read to its genomic neighbors. Given long enough reads, and short enough library fragments, these two reads can be merged informatically to make one long read that covers the entire fragment. Using the barcode sequence reads and the 9 nucleotide duplicated sequence present from the insertion, reads can now be linked to their genomic neighbors to form much longer "linked reads" in silico. As will be understood, a library comprising template nucleic acids can include duplicate nucleic acid fragments. Sequencing duplicate nucleic acid fragments is advantageous in methods that include creating a consensus sequence for duplicate fragments. Such methods can increase the accuracy for providing a consensus sequence for a template nucleic acid and/or library of template nucleic acids.

In some embodiments, sequence analysis is performed in real time, for example, sequence data can be obtained and simultaneously analyzed. In some embodiments, a sequencing process to obtain sequencing data can be terminated at various points, including after at least a portion of a target nucleic acid sequence data is obtained or before the entire nucleic acid read is sequenced. Exemplary methods, systems, and further embodiments are provided in International Patent Application Publication No WO 2010/062913, the contents of which are incorporated herein in its entirety.

Figure 6:
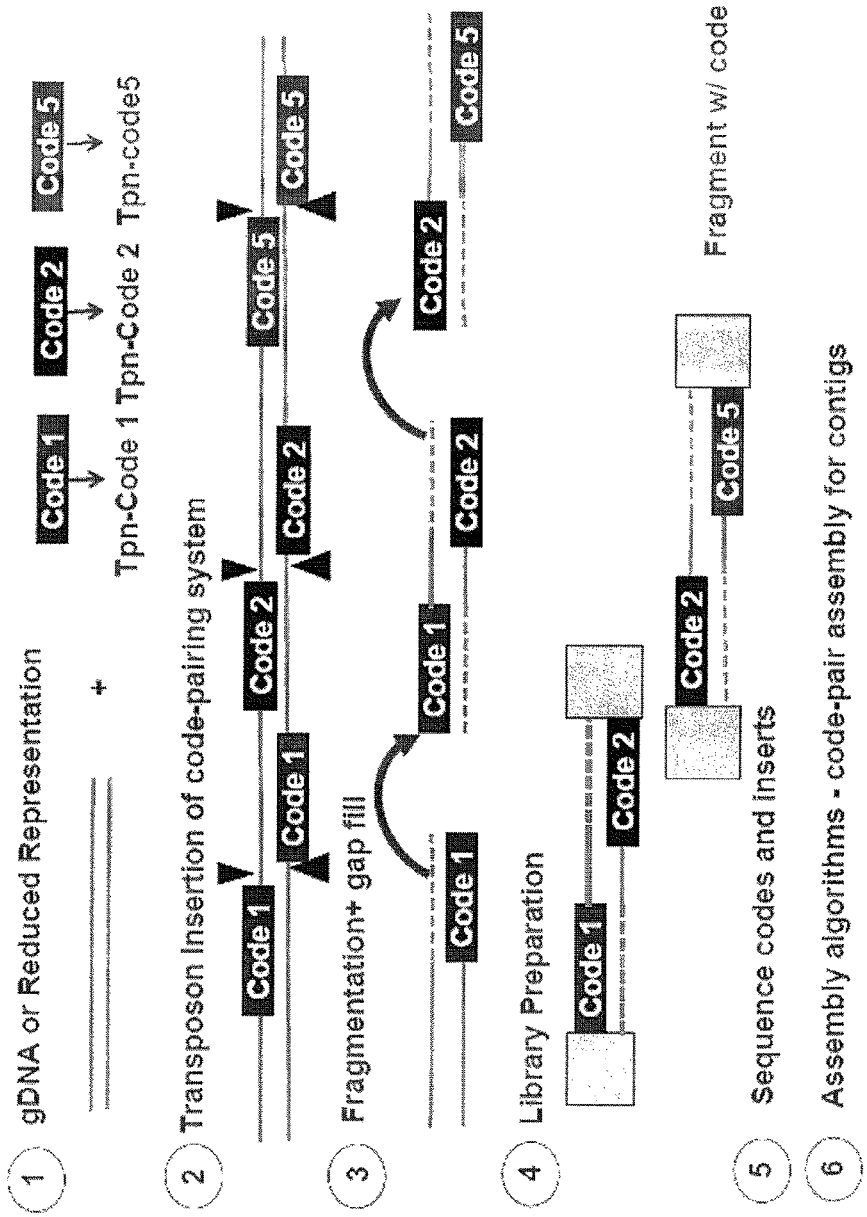
FIG. 6 depicts a schematic representation of using paired bar codes (indicated by Code 1, Code 2, Code 5) for code-pair sequencing of template contig sequences to assemble the sequence of an original target nucleic acid.
Figure 7:
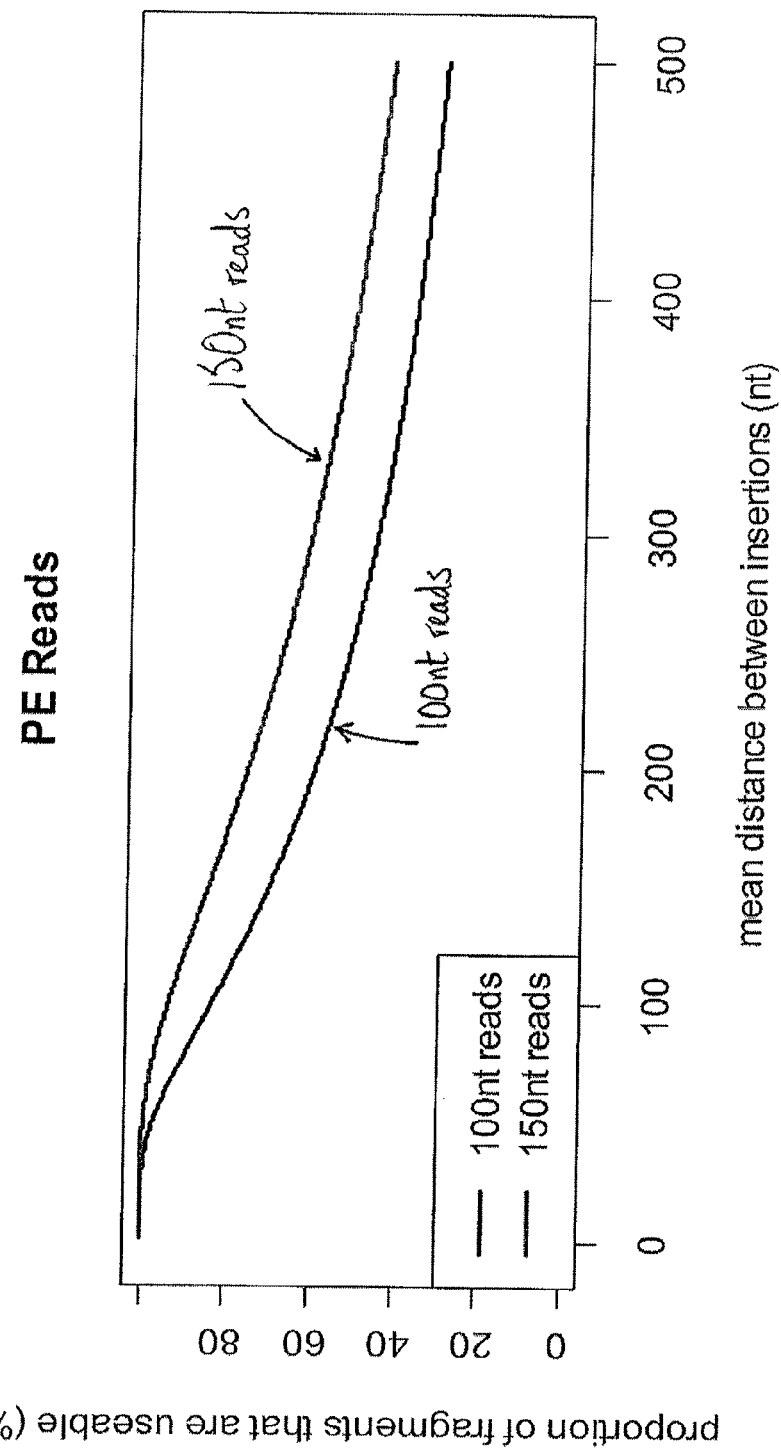
FIG. 7 depicts a graph showing that the proportion of template nucleic acids that are useful can decrease as the average distance between sites of integration increases.
Figure 8:
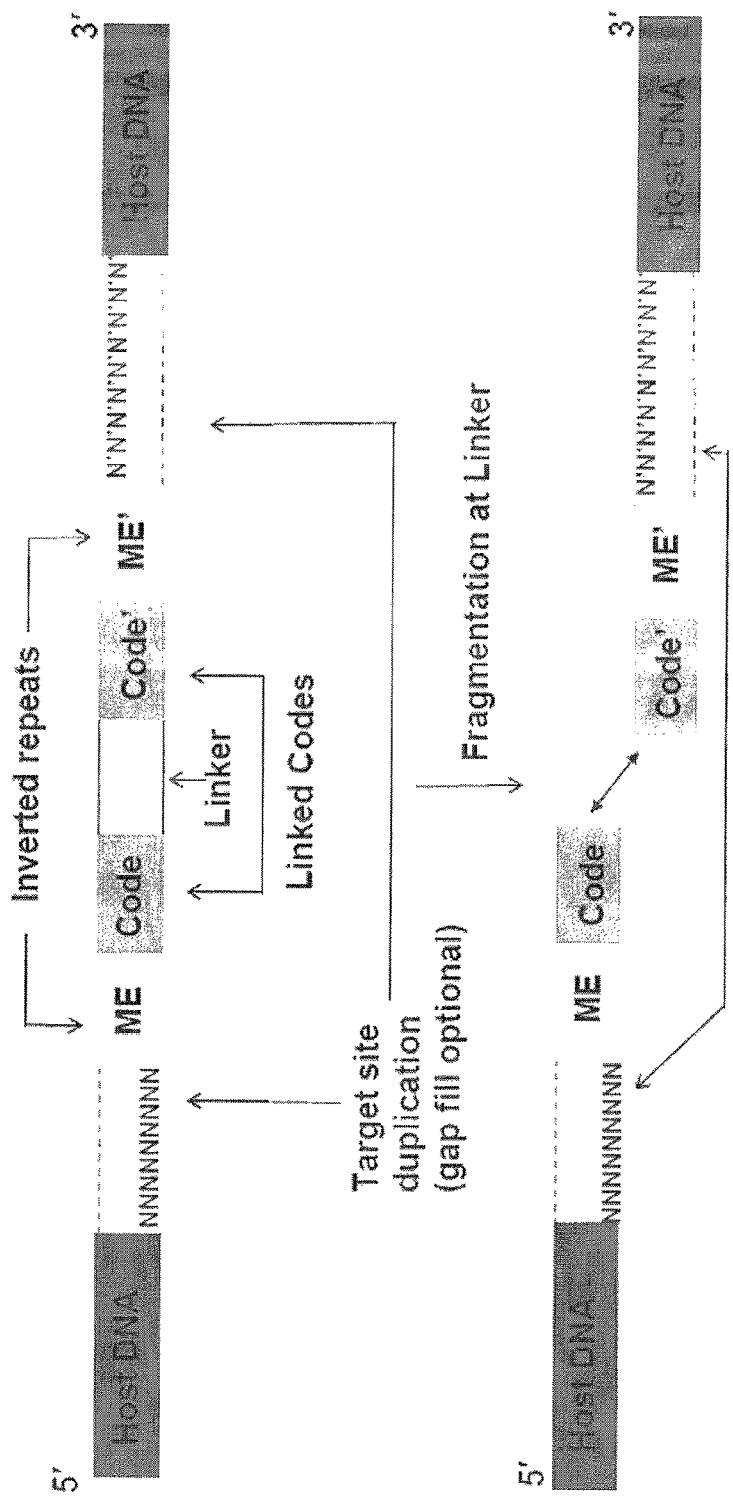
FIG. 8 depicts an exemplary embodiment of a method including fragmentation.
Figure 9:
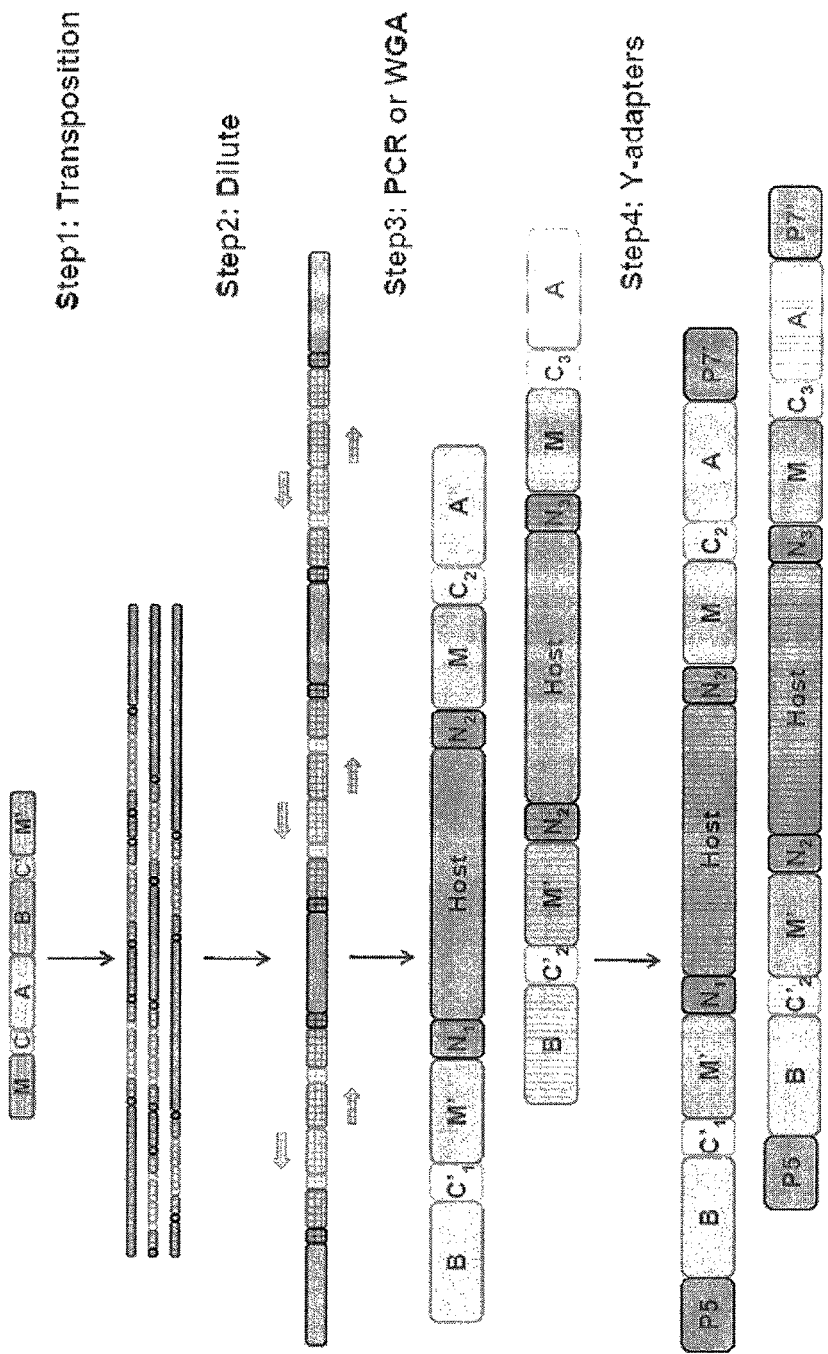
FIG. 9 depicts an exemplary embodiment of a method that includes optional steps of amplifying a target nucleic acid by PCR or whole genome amplification (WGA). In this figure, the filled-in region is indicated by $N_1$ and $N_2$.
Figure 10:
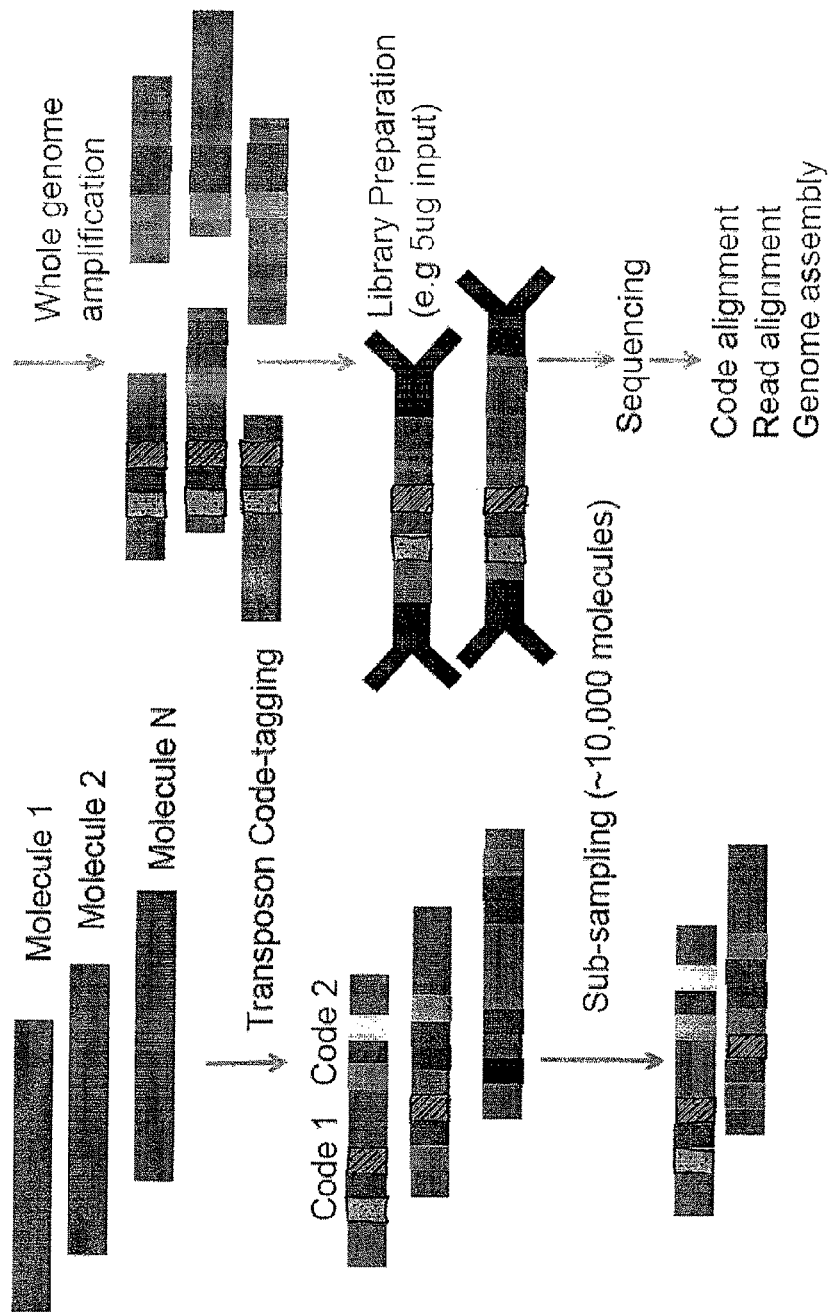
FIG. 10 depicts an exemplary embodiment of a method for assembling short sequencing reads using a linked read strategy. Optional steps of sub-sampling, code alignment, read assembly, and genome assembly are also illustrated.

FIG. 6 depicts an exemplary embodiment of a method for assembling short sequencing reads using a linked read strategy. In such an exemplary embodiment, transposon sequences comprising barcodes are inserted into genomic DNA, a library is prepared and sequencing data obtained for the library of template nucleic acids. Blocks of templates are assembled by identifying paired barcodes and larger contigs are then assembled. FIG. 8, FIG. 9 and FIG. 10 depict exemplary embodiments of methods of assembling sequencing reads using a linked ready strategy.

Some embodiments include error detection and correction. Examples of errors can include errors in base calls during a sequencing process, and errors in assembling fragments into larger contigs. As would be understood, error detection can include detecting the presence or likelihood of errors in a data set, and as such detecting the location of an error or number of errors may not be required. For error correction, information regarding the location of an error and/or the number of errors in a data set is useful. Methods for error correction are well known in the art. Examples include the use of hamming distances, and the use of a checksum algorithm (See, for example, U.S. Patent Application No. 20100323348; U.S. Pat. No. 7,574,305; U.S. Pat. No. 6,654,696, which are each incorporated herein by reference in their entireties)

Sequencing Methods

The methods described herein can be used in conjunction with a variety of sequencing techniques. In some embodiments, the process to determine the nucleotide sequence of a target nucleic acid can be an automated process.

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another example type of SBS, cycle sequencing is accomplished by stepwise addition of reversible terminator nucleotides containing, for example, a cleavable or photobleachable dye label as described, for example, in U.S. Pat. No. 7,427,67, U.S. Pat. No. 7,414,1163 and U.S. Pat. No. 7,057,026, the disclosures of which are incorporated herein by reference. This approach is being commercialized by Solexa (now Illumina Inc.), and is also described in WO 91/06678 and WO 07/123744 (filed in the United States patent and trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Additional example SBS systems and methods which can be utilized with the methods and systems described herein are described in U.S. Patent Application Publication No. 2007/0166705, U.S. Patent Application Publication No. 2006/

0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010251, the disclosures of which are incorporated herein by reference in their entireties.

Some embodiments can utilize sequencing by ligation techniques. Such techniques utilize DNA ligase to incorporate nucleotides and identify the incorporation of such nucleotides. Example SBS systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

Some embodiments can include techniques such as next-next technologies. One example can include nanopore sequencing techniques (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis". *Acc. Chem. Res.* 35:817-825 (2002); Li, J., M. Gershow, D. Stein, E. Brandin, and J. A. Golovchenko, "DNA molecules and configurations in a solid-state nanopore microscope" *Nat. Mater.* 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53, 1996-2001 (2007); Healy, K. "Nanopore-based single-molecule DNA analysis." *Nanomed.* 2, 459-481 (2007); Cockroft, S. L., Chu, J., Amorin, M. & Ghadiri, M. R. "A single-molecule nanopore device detects DNA polymerase activity with single-nucleotide resolution." *J. Am. Chem. Soc.* 130, 818-820 (2008), the disclosures of which are incorporated herein by reference in their entireties). In some such embodiments, nanopore sequencing techniques can be useful to confirm sequence information generated by the methods described herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. No. 7,329,492 and U.S. Pat. No. 7,211,414 (each of which is incorporated herein by reference in their entireties) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 and U.S. Patent Application Publication No. 2008/0108082 (each of which is incorporated herein by reference in their entireties). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299, 682-686 (2003); Lundquist, P. M. et al. "Parallel confocal detection of single molecules in real time." *Opt. Lett.* 33, 1026-1028 (2008); Korlach, J. et al. "Selective aluminum passivation for targeted immobilization of single DNA polymerase molecules in zero-mode waveguide nanostructures." *Proc. Natl. Acad. Sci. USA* 105, 1176-1181 (2008), the disclosures of which are incorporated herein by reference in their entireties). In one example single molecule, real-time (SMRT) DNA sequencing technology provided by Pacific Biosciences Inc can be utilized with the methods described herein. In some embodiments, a SMRT chip or the like may be utilized (U.S. Pat. Nos. 7,181,122, 7,302,146, 7,313,308, incorporated by reference in their entireties). A SMRT chip comprises a plurality of zero-mode waveguides (ZMW). Each ZMW comprises a cylindrical hole tens of nanometers in diameter perforating a thin metal film supported by a transparent substrate. When the ZMW is illuminated through the transparent substrate, attenuated light may penetrate the lower 20-30 nm of each ZMW creating a detection volume of about $1 \times 10^{-21}$ L. Smaller detection volumes increase the sensitivity of detecting fluorescent signals by reducing the amount of background that can be observed.

SMRT chips and similar technology can be used in association with nucleotide monomers fluorescently labeled on the terminal phosphate of the nucleotide (Korlach J. et al., "Long, processive enzymatic DNA synthesis using 100% dye-labeled terminal phosphate-linked nucleotides." Nucleosides, Nucleotides and Nucleic Acids, 27:1072-1083, 2008; incorporated by reference in its entirety). The label is cleaved from the nucleotide monomer on incorporation of the nucleotide into the polynucleotide. Accordingly, the label is not incorporated into the polynucleotide, increasing the signal:background ratio. Moreover, the need for conditions to cleave a label from labeled nucleotide monomers is reduced.

An additional example of a sequencing platform that may be used in association with some of the embodiments described herein is provided by Helicos Biosciences Corp. In some embodiments, TRUE SINGLE MOLECULE SEQUENCING can be utilized (Harris T. D. et al., "Single Molecule DNA Sequencing of a viral Genome" Science 320: 106-109 (2008), incorporated by reference in its entirety). In one embodiment, a library of target nucleic acids can be prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid. In one embodiment, fluorescently-labeled nucleotide monomer, namely, A, C, G, or T, are delivered one at a time to the target nucleic acid in the presence DNA polymerase. Incorporation of a labeled nucleotide into the polynucleotide complementary to the target nucleic acid is detected, and the position of the fluorescent signal on the glass cover slip indicates the molecule that has been extended. The fluorescent label is removed before the next nucleotide is added to continue the sequencing cycle. Tracking nucleotide incorporation in each polynucleotide strand can provide sequence information for each individual target nucleic acid.

An additional example of a sequencing platform that can be used in association with the methods described herein is provided by Complete Genomics Inc. Libraries of target nucleic acids can be prepared where target nucleic acid sequences are interspersed approximately every 20 bp with adaptor sequences. The target nucleic acids can be amplified using rolling circle replication, and the amplified target nucleic acids can be used to prepare an array of target nucleic acids. Methods of sequencing such arrays include sequencing by ligation, in particular, sequencing by combinatorial probe-anchor ligation (cPAL).

In some embodiments using cPAL, about 10 contiguous bases adjacent to an adaptor may be determined. A pool of probes that includes four distinct labels for each base (A, C, T, G) is used to read the positions adjacent to each adaptor. A separate pool is used to read each position. A pool of probes and an anchor specific to a particular adaptor is delivered to the target nucleic acid in the presence of ligase. The anchor hybridizes to the adaptor, and a probe hybridizes to the target nucleic acid adjacent to the adaptor. The anchor and probe are ligated to one another. The hybridization is detected and the anchor-probe complex is removed. A different anchor and pool of probes is delivered to the target nucleic acid in the presence of ligase.

The sequencing methods described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically coupled to a surface in a spatially distinguishable manner. For example, the target nucleic acids can be bound by direct covalent attachment, attachment to a bead or other particle or associated with a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, 10$^7$ features/cm$^2$, 5×10$^7$ features/cm$^2$, 10$^8$ features/cm$^2$, 5×10$^8$ features/cm$^2$, 10$^9$ features/cm$^2$, 5×10$^9$ features/cm$^2$, or higher.

Surfaces

In some embodiments, the nucleic acid template provided herein can be attached to a solid support ("substrate"). Substrates can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Various methods can be used to attach, anchor or immobilize nucleic acids to the surface of the substrate. The immobilization can be achieved through direct or indirect bonding to the surface. The bonding can be by covalent linkage. See, Joos et al. (1997) Analytical Biochemistry, 247:96-101; Oroskar et al. (1996) Clin. Chem., 42:1547-1555; and Khandjian (1986) Mol. Bio. Rep., 11:107-11. A preferred attachment is direct amine bonding of a terminal nucleotide of the template or the primer to an epoxide integrated on the surface. The bonding also can be through non-covalent linkage. For example, biotin-streptavidin (Taylor et al. (1991) J. Phys. D: Appl. Phys., 24:1443,) and digoxigenin with anti-digoxigenin (Smith et al. (1992) Science, 253:1122, are common tools for anchoring nucleic acids to surfaces and parallels. Alternatively, the attachment can be achieved by anchoring a hydrophobic chain into a lipid monolayer or bilayer. Other methods known in the art for attaching nucleic acid molecules to substrates can also be used.

EXAMPLE APPLICATIONS

Some embodiments include the use of the compositions and methods provided herein in single cell applications. In some embodiments, a transposon sequence can be associated with a bead via a cleavable linker. A bead comprising the transposon sequence and transposase is provided in a droplet. The cell is lysed and the transposon sequence cleaved from the bead. The transposition reaction is intiated. Such methods can be used to provide a library of template nucleic acids for each cell in population.

The following Examples provide illustrative embodiments and do not in any way limit the inventions provided herein.

EXAMPLES

Example 1

Whole Genome Amplification Using Transposon Sequences

This example illustrates a method for uniform amplification of genomic DNA with random insertion therein of specific primer sites. Transposon sequences are prepared, each comprising a first transposase recognition site, a second transposase recognition site having a sequencing adaptor disposed therebetween, in which the sequencing adaptor comprises a first primer site and second primer site. The transposon sequences are contacted with genomic DNA in the presence of MuA transposase under conditions sufficient for the transposon sequences to integrate into the genomic DNA. The genomic DNA is amplified using primers that hybridize to the first primer site or second primer site.

Example 2

Landmark Sequencing Methods Using Genomes with Increased Complexity

This example illustrates an embodiment for providing additional markers in a genome. Additional markers can be useful in genomes that include repetitive sequences during subsequent assembly steps to generate a sequence representation of the genome. Transposon sequences are prepared, each comprising a different barcode. The transposon sequences are integrated into genomic DNA in a transposition reaction. The genomic DNA comprising the integrated transposon is amplified by whole genome amplification. A sequencing library is prepared from the amplified template nucleic acids. Sequencing data is obtained from the sequencing library. Sequencing reads can include representations of one or more nucleic acids with the same barcode on each nucleic acid. Such nucleic acids are identified as containing sequences that overlap in a sequence representation of the genomic DNA. The sequencing reads can be assembled by identifying barcodes on overlapping sequences.

Example 3

Predicted Average Coverage Using Linked Read Sequencing Strategy

Useable fragment lengths are modeled as a truncated exponential distribution so that the mean useable fragment length can be obtained by setting k=b/d, where d is the mean of the non-truncated exponential (the total fragment distribution) and b is the value for truncation (either 180 or 280 for 100 nucleotides and 150 nucleotide paired-end reads, respectively) and then calculating the mean of the truncated exponential as $$E(f)=d(1-(k+1)e^{-k})/(1-e^{-k})$$

The proportion of useable reads is $p=C(b)\times(1-D(0,T))$ where C is the exponential cumulative distribution function, T is the average repetitions of observing each fragment (num clusters)/complexity, complexity is the genome size times the number of genome copies diluted to divided by d, and D is the Poisson cumulative distribution function Expected length of linked read is then $(E(f)-9)\times 1/(1-p)+9$ where p is proportion of useable reads: 9 is subtracted from each read because of the reused 9 nucleotides sequence in neighboring fragments; and 9 nucleotides is added back to the linked read to account for the end read—one of its 9 nucleotides segments is not shared with another read within the linked read.

The distribution of linked read lengths is also exponential with the above expected value. Very long linked reads can be observed.

Table 1 sets out predicted average coverage for a bacterial genome, human PCR product, and a single copy of a human diploid genome using a linked read strategy.

TABLE 1

| Target nucleic acid | Genome size | Read length | Diluted copies | Number of clusters | Average insert distance | Average coverage | Mean linked read length |
|---|---|---|---|---|---|---|---|
| Bacterial genome | 5.0e6 | 150 | 10 | 35,000,000 | 50 nt | 9.96 X | 10,815 nt |
| Human PCR product | 20 kb | 150 | 10,000 | 40,000,000 | 50 nt | 9.96 X | 10,811 nt |
| Single cell, human diploid genome | 3e9 | 150 | 2 | 3000,000,000 | 50 nt | 9.66 X | 1,191 nt |

Example 4

De Novo Sequencing Target DNA

This example illustrates an embodiment of assembling sequencing data obtained from a library of template nucleic acids prepared from a target DNA.

A plurality of transposon sequences are integrated into the target DNA in a transposition reaction. Each transposon sequence includes a barcode which comprises a first barcode sequence and a second barcode sequence. The first barcode sequence is the reverse complement of the second barcode sequence. There are more than $10^{18}$ different barcodes in the plurality of transposon sequences, such that the code space is large and out-competes the complexity of the target DNA. Accordingly, each integrated barcode is likely to be unique. Optionally, the target DNA comprising the integrated transposon sequences is sub-sampled. The sub-sampled target DNA comprising the integrated transposon sequences is amplified by methods of whole genome amplification. A sequencing library is prepared from the amplified nucleic acids. Sequencing data is obtained from the sequencing library. The sequencing data comprises sequencing reads for each amplified nucleic acid.

Sequencing reads that include a barcode sequence that can be paired with a barcode sequence of another sequencing read are aligned. Shorter alignments of sequencing reads are aligned with other short alignments by identifying paired barcode sequences to produce longer alignments. A sequence representation of the target DNA is generated.

Example 5

Preparing a Linked Library with Blunt-End Barcodes

This example illustrates an embodiment of preparing a linked library that includes identical barcodes on template nucleic acids that include adjacent sequences in a sequence representation of the target nucleic acid.

Transposon sequences are prepared comprising a first fragmentation site and a second fragmentation site, having a barcode disposed therebetween. Each fragmentation site comprises a site that can be nicked to produce a single-stranded sticky end, e.g., a restriction endonuclease site that produces a single-strand sticky end. The transposon sequences are integrated into the target DNA by a transposition reaction. Optionally, the target DNA comprising the integrated transposon sequences is sub-sampled. The sub-sampled target DNA comprising the integrated transposon sequences is amplified by methods of whole genome amplification. The amplified nucleic acids are fragmented at the first and second fragmentation sites at each integrated transposon sequence to generate nucleic acids comprising sticky ends. The sticky ends are filled-in so that each end comprises a barcode. Adaptors are ligated to the blunt ends of each nucleic acid. The nucleic acids are amplified using primer sites of the adaptors.

A sequencing library is prepared from the amplified nucleic acids. Sequencing data is obtained from the sequencing library. The sequencing data comprises sequencing reads for each amplified nucleic acid. Sequencing reads that include a barcode sequence that can be paired with a barcode sequence of another sequencing read are aligned. Shorter alignments of sequencing reads are aligned with other short alignments by identifying paired barcode sequences to produce longer alignments. A sequence representation of the target DNA is generated.

Figure 11:
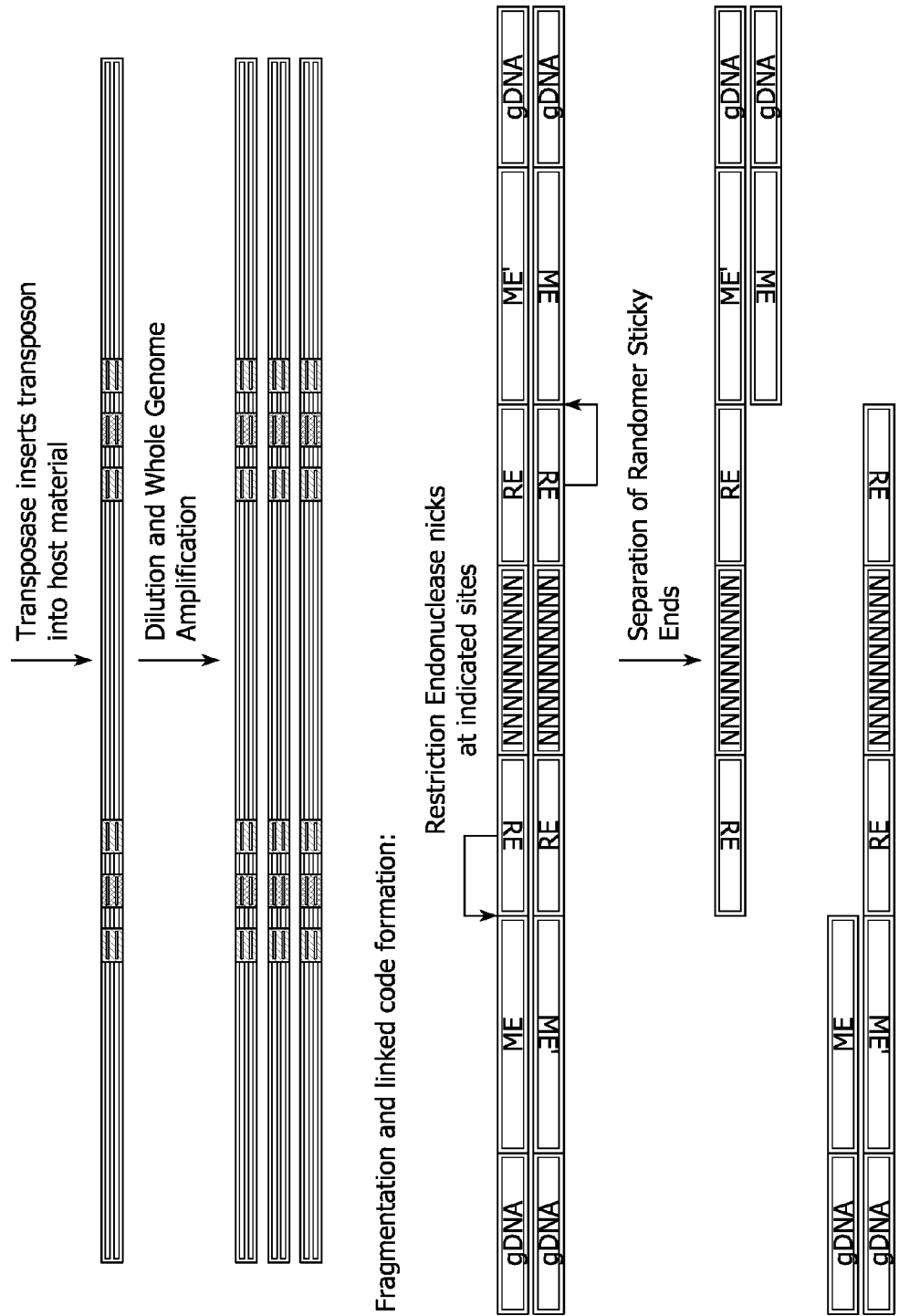
FIG. 11 depicts an embodiment using restriction endonucleases to generate randomer sticky ends. Steps include: transposase inserts transposon into host material; dilution and whole genome amplification; fragmentation and linked code formation; restriction endonuclease nicks at indicated sites; and separation of randomer sticky ends.

An exemplary embodiment of this method is depicted in FIGS. 11 and 12. FIG. 11 depicts the insertion of the transposon sequence into the target nucleic acid (host material), dilution of the template nucleic acids, and subsequent whole genome amplification of the template nucleic acids. The amplified template nucleic acids are fragmented in the presence of a restriction endonuclease that nicks the transposon sequences at the first restriction endonuclease site and the second restriction endonuclease site to yield two sticky ends. FIG. 12 depicts a fill-in reaction of the sticky ends, followed by A-tailing the ends and adding adaptors to the tailed ends. The adaptors can be used in subsequent amplification, library preparation, and methods to obtain sequence data. In other embodiments, the fill-in reaction itself can be used as part of a detection assay, such as by incorporating detectably labeled nucleotides in a variety of assay formats. Advantageously, methods that utilize a nicking endonuclease may be carried out with a relatively small number of target nucleic acids, or a relatively dilute concentration of the target nucleic acid.

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. For example, the invention has been exemplified using nucleic acids but can be applied to other polymers as well. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method of sequencing a target nucleic acid, comprising:
   (a) contacting a target nucleic acid with a plurality of transposons under conditions such that a plurality of the transposons are inserted into the target nucleic acid,
   wherein the transposons that are inserted into the target nucleic acid each comprise a first transposase recognition site, a second transposase recognition site, and a barcode pair,
   wherein the barcode pair comprises a first barcode sequence, a second barcode sequence and a linker comprising a fragmentation site disposed between the first and second barcode sequences, wherein the first barcode sequence comprises a first strand and a second strand that is not complementary to the first strand of the first barcode sequence,
   wherein the barcode pair is disposed between the first and second transposase recognition sites;
   (b) fragmenting the target nucleic acid at the fragmentation sites thereby preparing a library of template nucleic acid fragments;
   (c) obtaining sequence reads from the nucleic acid fragments; and
   (d) assembling a representation of at least a portion of the target nucleic acid from the sequence reads, wherein the assembling comprises determining the order of the sequence reads from the identities of the first barcode sequence and the second barcode sequence of each barcode pair.

2. The method of claim 1, wherein the target nucleic acid comprises cDNAs from a single cell.

3. The method of claim 1, wherein the target nucleic acid comprises nucleic acids from a plurality of species.

4. The method of claim 1, wherein the target nucleic acid comprises nucleic acids from a plurality of haplotypes.

5. The method of claim 1, wherein the fragmentation site comprises an enzyme cleavage site selected from the group consisting of a restriction endonuclease recognition sequence, a nickase recognition sequence, and a ribonucleotide sequence.

6. The method of claim 5, wherein the fragmentation site is a restriction endonuclease site and wherein fragmentation comprises fragmenting the target nucleic acid with a restriction endonuclease enzyme that recognizes the restriction endonuclease recognition site.

7. The method of claim 5, wherein the fragmentation site is a nickase recognition site and wherein fragmentation comprises fragmenting the target nucleic acid with a nickase enzyme that recognizes the nickase recognition sequence.

8. The method of claim 1, wherein the second barcode sequence of the barcode pair is different from the first barcode sequence of the barcode pair.

9. The method of claim 1, wherein the second barcode sequence comprises a first strand and a second strand that is not complementary to the first strand of the second barcode sequence.

10. The method of claim 1, wherein at least 90% of the barcode pairs in the plurality of transposons are different from each other.

11. A method of sequencing a target nucleic acid comprising:
   (a) contacting a target nucleic acid with a plurality of transposons under conditions such that a portion of the transposons are inserted into the target nucleic acid, wherein the transposons that are inserted into the target nucleic acid each comprise a first transposase recognition site, a second transposase recognition site, and a barcode pair,
   wherein the barcode pair comprises a first barcode sequence, a second barcode sequence and a linker comprising a first primer site disposed between the first and second barcode sequences, wherein the first barcode sequence comprises a first strand and a second strand that is not complementary to the first strand of the first barcode sequence,
   wherein the barcode pair is disposed between the first and second transposase recognition sites;
   (b) hybridizing a first primer to the first primer site;
   (c) amplifying a portion of the transposon using the first primer that is hybridized to the first primer site, to create a plurality of amplified nucleic acids for sequencing;
   (d) obtaining sequence reads from the amplified nucleic acids; and
   (e) assembling a representation of at least a portion of the target nucleic acid from the sequence reads, wherein the assembling comprises determining the order of the sequence reads from the identities of the first barcode sequence and the second barcode sequence of each barcode pair.

12. The method of claim 11, wherein the assembling further comprises identifying the presence of a first barcode sequence in one sequencing read and the presence of a second barcode sequence in another sequencing read, thereby indicating proximity between the two sequencing reads in the target nucleic acid.

13. The method of claim 12, wherein step (d) is terminated after the first and second barcode sequences are identified.

14. The method of claim 11, wherein the linker further comprises a second primer site and the method further comprises hybridizing a second primer to the second primer site.

15. The method of claim 14, wherein the amplifying of the portion of the transposon uses both the first primer that is hybridized to the first primer site and the second primer that is hybridized to the second primer site.

16. The method of claim 11, wherein the second barcode sequence of the barcode pair is different from the first barcode sequence of the barcode pair.

17. The method of claim 11, wherein the second barcode sequence comprises a first strand and a second strand that is not complementary to the first strand of the second barcode sequence.

18. The method of claim 11, wherein at least 90% of the barcode pairs in the plurality of transposons are different from each other.

19. A method of sequencing a target nucleic acid, comprising:
   (a) contacting a target nucleic acid with a plurality of transposons under conditions such that a plurality of the transposons are inserted into the target nucleic acid, wherein the transposons that are inserted into the target nucleic acid each comprise a first transposase recognition site, a second transposase recognition site, and a barcode pair,
   wherein the barcode pair comprises a first barcode sequence, a second barcode sequence and a linker comprising a fragmentation site disposed between the first and second barcode sequences, wherein the fragmentation site is a ribonucleotide sequence and wherein fragmentation comprises fragmenting the target nucleic acid with a RNAse,
   wherein the barcode pair is disposed between the first and second transposase recognition sites;
   (b) fragmenting the target nucleic acid at the fragmentation sites thereby preparing a library of template nucleic acid fragments;
   (c) obtaining sequence reads from the nucleic acid fragments; and
   (d) assembling a representation of at least a portion of the target nucleic acid from the sequence reads, wherein the assembling comprises determining the order of the sequence reads from the identities of the first barcode sequence and the second barcode sequence of each barcode pair.

20. The method of claim 19, wherein the target nucleic acid comprises cDNAs from a single cell.

21. The method of claim 19, wherein the target nucleic acid comprises nucleic acids from a plurality of species.

22. The method of claim 19, wherein the target nucleic acid comprises nucleic acids from a plurality of haplotypes.

* * * * *